United States Patent [19]

Neurath et al.

[11] Patent Number: 5,985,313
[45] Date of Patent: Nov. 16, 1999

[54] METHOD FOR DECREASING THE FREQUENCY OF TRANSMISSION OF VIRAL INFECTIONS USING CELLULOSE ACETATE PHTHALATE OR HYDROXYPROPYL METHYLCELLULOSE PHTHALATE EXCIPIENTS

[75] Inventors: Alexander Robert Neurath, New York, N.Y.; Asim Kumar Debnath, Fort Lee, N.J.; Shibo Jiang, New York; Nathan Strick, Oceanside, both of N.Y.; Gordon Jay Dow, Santa Rosa, Calif.

[73] Assignee: New York Blood Center, Inc., New York, N.Y.

[21] Appl. No.: 09/112,130

[22] Filed: Jul. 8, 1998

Related U.S. Application Data

[60] Provisional application No. 60/062,936, Oct. 22, 1997, and provisional application No. 60/071,017, Jan. 13, 1998.

[51] Int. Cl.$^6$ .............................. A61F 13/02; A61F 6/06; A61F 6/14; A61K 9/16
[52] U.S. Cl. ......................... 424/434; 424/430; 424/431; 424/432; 424/433; 424/435; 424/436; 424/443; 424/494
[58] Field of Search ..................................... 424/430, 431, 424/432, 433, 434, 435, 436, 443, 494

[56] References Cited

U.S. PATENT DOCUMENTS

| | | |
|---|---|---|
| 4,330,338 | 5/1982 | Banker . |
| 4,385,078 | 5/1983 | Onda et al. . |
| 4,462,839 | 7/1984 | McGinley et al. . |
| 4,518,433 | 5/1985 | McGinley et al. . |
| 4,960,814 | 10/1990 | Wu et al. . |
| 4,968,350 | 11/1990 | Bindschaedler et al. . |
| 5,025,004 | 6/1991 | Wu et al. . |
| 5,326,572 | 7/1994 | Mehra et al. . |
| 5,356,634 | 10/1994 | Wu et al. . |
| 5,380,790 | 1/1995 | Chen et al. . |
| 5,512,092 | 4/1996 | Maruyama et al. . |
| 5,646,151 | 7/1997 | Kruse et al. ............................ 514/255 |
| 5,723,151 | 3/1998 | Cook et al. . |

OTHER PUBLICATIONS

Neurath, et al., "3–Hydroxyphtaloyl–β–lactoglobulin. I. Optimization of production and comparison with other compounds considered for chemoprophylaxis of mucosally transmitted human immunodeficiency virus type 1", *Antiviral Chemistry & Chemotherapy*, 1196, vol. 8(2), pp. 131–139.

Neurath, et al., "3–Hydroxyphthaloyl–β–lactoglobulin. II. Anti–human immunodeficiency virus type 1 activity in in vitro environments relevant to prevention of sexual transmission of the virus", *Antiviral Chemistry & Chemotherapy*, 1997, vol. 8(2); pp. 141–148.

Neurath, et al., "A herpesvirus inhibitor from bovine whey", *The Lancet*, vol. 347, Jun. 15, 1996, p. 1703.

Jiang, et al., "Virucidal and Antibacterial Activities of 3–HP–β–LG", 1997, *Vaccines 97*, pp. 327–330.

Jiang, et al, Chemically Modified Bovine β–Lactoglobulin Blocks Uptake of HIV–1 by Colon–and Cervix–Derived Epithelial Cell Lines, *Journal of Acquired Immune Deficiency Syndromes and Human Retrovirology*, 1996, vol. 13, pp. 461–462.

Neurath, et al., "Bovine β–lactoglobulin modified by 3–hydroxyphthalic anhydride blocks the CD 4 cell receptor for HIV", *Nature Medicine*, vol. 2, No. 2, 2–1996, pp. 230–234.

*Primary Examiner*—Carlos Azpuru
*Attorney, Agent, or Firm*—Frishauf, Holtz, Goodman, Langer & Chick, P.C.

[57] ABSTRACT

A method for decreasing the frequency of transmission of human immunodeficiency virus or herpesviruses by administering to a human an anti-human immunodeficiency virus amount or an anti-herpesvirus amount of cellulose acetate phthalate (CAP) or hydroxypropyl methylcellulose phthalate (HPMCP), such as in micronized form, or a combination thereof, either alone or in combination with a pharmaceutically acceptable carrier or diluent. The CAP and/or HPMCP may be employed as a suspension of micronized particles and may further contain a water miscible, nonsolvent for CAP or HPMCP, such as glycerol.

32 Claims, 6 Drawing Sheets

METHOD FOR DECREASING THE FREQUENCY OF TRANSMISSION OF VIRAL INFECTIONS USING CELLULOSE ACETATE PHTHALATE OR HYDROXYPROPYL METHYLCELLULOSE PHTHALATE EXCIPIENTS

This appln. claims the benefit of U.S. Provisional No. 60/062,936, Oct. 22, 1997 and Provisional No. 60/071,017 filed Jan. 13, 1998.

BACKGROUND OF THE INVENTION

1. Field of the Invention

The present invention concerns methods for decreasing the frequency of transmission of viral infection, such as human immunodeficiency virus and herpesvirus, by administration of cellulose acetate phthalate or hydroxypropyl methylcellulose phthalate, which were heretofore employed as pharmaceutical excipients.

2. Background Information

Pharmaceutical excipients are defined as inert substances that form a vehicle for drug delivery (*Webster's Ninth New Collegiate Dictionary*, Merriam-Webster Inc. Publishers, Springfield, Mass., USA, 1985, p. 432). Thus, excipients convert pharmacologically active compounds into pharmaceutical dosage forms suitable for administration to patients. Some excipients are also used for the formulation or production of confectionery, cosmetics and food products. Therefore, approved excipients are used frequently and at higher dosage levels in comparison with most drugs. Excipients are also much less expensive and more easily produced in very large scale in comparison with most drugs.

Human immunodeficiency viruses ("HIV") have been known as the causative virus for AIDS (Acquired Immunodeficiency Syndrome). The prevalence of AIDS cases is presently increasing at an alarming rate.

Two related retroviruses that can cause AIDS are human immunodeficiency virus type 1 (HIV-1) and type 2 (HIV-2). The genomes of these two viruses are about 50% homologous at the nucleotide level, contain the same complement of genes, and appear to attack and kill the same human cells by the same mechanism.

HIV-1 was identified in 1983. Virtually all AIDS cases in the United States are associated with HIV-1 infection. HIV-2 was isolated in 1986 from West African AIDS patients.

HIV-1 and HIV-2 are retroviruses in which the genetic material is RNA, rather than DNA. The HIV-1 and HIV-2 viruses carry with them a polymerase (reverse transcriptase) that catalyzes transcription of viral RNA into double-helical DNA.

The viral DNA can exist as an unintegrated form in the infected cell or be integrated into the genome of the host cell. As presently understood, the HIV enters the T4 lymphocyte where it loses its outer envelope, releasing viral RNA and reverse transcriptase.

The reverse transcriptase catalyzes synthesis of a complementary DNA strand from the viral RNA template. The DNA helix then inserts into the host genome where it is known as the provirus. The integrated DNA may persist as a latent infection characterized by little or no production of virus or helper/inducer cell death for an indefinite period of time. When the viral DNA is transcribed and translated by the infected lymphocyte, new viral RNA and proteins are produced to form new viruses that bud from the cell membrane and infect other cells.

Attempts to treat AIDS with drugs which inhibit reverse transcriptase such as 3'-azido-3'-deoxythymidine (AZT) have not been met with a desirable degree of success. Moreover, there is a potential for toxicity with the use of anti-viral drugs. Thus there is a need for an effective and safe means to prevent and treat AIDS.

HIV infections are transmitted by means such as contaminated intravenous drug needles and through sexual contact. Sexual transmission is the most frequent (86%) route of adult HIV-1 infections worldwide (*AIDS in the World*, Harvard University Press, Cambridge, Mass., (1992)).

The transmission of HIV by heterosexual sex poses an especially severe problem for women. By the year 2,000, it is estimated that 90% of HIV infections will be acquired via heterosexual intercourse.

The utilization of condoms provides a substantial degree of protection against transmission of HIV and herpesvirus infections during sexual intercourse, but a difficulty arises when condoms are not employed. Moreover, the use of condoms appears to be a culturally and socially unacceptable practice in many countries.

Although men can protect themselves from sexually transmitted HIV and herpesvirus infection by using condoms, women who are sexually active have no similar means. Women can encourage their male sex partners to use a condom, but may not succeed. The female condom, which is just becoming available, is expensive and there is presently no evidence that it prevents sexual transmission of HIV or herpesvirus.

Even maintaining a monogamous sexual relationship is no guarantee of safety, for if a woman's male partner becomes infected, he can pass the virus to her. And as more women are infected, so are more babies.

There is presently frustration in the medical field by the bleak prospect for an effective AIDS vaccine in the near future and the severe limitations of drugs that effectively and safely combat HIV.

Due to the present absence of a prophylactic anti-HIV vaccine and because of limitations of educational programs, other preventive methods have been sought. Spermicides with virucidal properties have been considered for this purpose, but their application is contraindicated by adverse effects (Bird, K. D., "The Use of Spermicide Containing Nonoxynol-9 in the Prevention of HIV Infection", *AIDS*, 5, 791–796 (1991)).

Anti-HIV drugs currently in use or expected to be clinically applied in the near future (Steele, F., "AIDS Drugs Lurch Towards Market", *Nature Medicine*, 1, 285–286 (1995)) are mostly not targeted to the earliest steps in the virus replicative cycle, lead to the emergence of drug resistant mutants, and are expensive, suggesting that their application for wide use in topical chemoprophylaxis is unlikely.

Cells which are the primary targets for sexual and mucosal transmission of HIV, either in the form of free virus or virus-infected cells, have not been fully defined and may be diverse (Miller, C. J. et al., "Genital Mucosal Transmission of Simian Immunodeficiency Virus: Animal Model for Heterosexual Transmission of Human Immunodeficiency Virus", *J. Virol.*, 63, 4277–4284 (1989); Phillips, D. M. and Bourinbaiar, A. S., "Mechanism of HIV Spread from Lymphocytes to Epithelia", *Virology*, 186, 261–273 (1992); Phillips, D. M., Tan, X., Pearce-Pratt, R. and Zacharopoulos, V. R., "An Assay for HIV Infection of Cultured Human Cervix-derived Cells", *J. Virol. Methods*, 52, 1–13 (1995); Ho, J. L. et al., "Neutrophils from Human Immunodeficiency Virus (HIV)-SeronegatiVe Donors Induce HIV Replication from HIV-infected Patients Mononuclear Cells and Cell lines": An In Vitro Model of HIV Transmission Facilitated by Chlamydia Trachomatis., "J. Exp. Med., 181, 1493–1505 (1995); and Braathen, L. R. & Mork, C. in "HIV infection of Skin Langerhans Cells", In: *Skin Langerhans (dendritic) cells in virus infections and AIDS* (ed. Becker, Y.) 131–139 (Kluwer Academic Publishers, Boston, (1991)). Such cells include T lymphocytes, monocytes/macrophages and dendritic cells, suggesting that CD4 cell receptors are engaged in the process of virus transmission (Parr, M. B. and Parr, E. L., "Langerhans Cells and T lymphocyte Subsets in the Murine Vagina and Cervix", *Biology of Reproduction*, 44, 491–498 (1991); Pope, M. et al., "Conjugates of Dendritic Cells and Memory T Lymphocytes from Skin Facilitate Productive Infection With HIV-1", *Cell*, 78, 389–398 (1994); and Wira, C. R. and Rossoll, R. M., "Antigen-presenting Cells in the Female Reproductive Tract: Influence of Sex Hormones on Antigen Presentation in the Vagina", *Immunology*, 84, 505–508 (1995)).

Therefore agents blocking HIV-CD4 binding are expected to diminish or prevent virus transmission. Soluble recombinant CD4 cannot be considered for this purpose since high concentrations are required to neutralize the infectivity of primary HIV isolates (Daar, E. S., Li, X. L., Moudgil, T. and Ho, D. D., "High Concentrations of Recombinant Soluble CD4 are Required to Neutralize Primary Human Immunodeficiency Virus Type 1 Isolates", *Proc. Natl. Acad. Sci. U.S.A.*, 87, 6574–6578 (1990), and in the case of SIV, the infectivity is enhanced by CD4 (Werner, A., Winskowsky, G. and Kurth, R., "Soluble CD4 Enhances Simian Immunodeficiency Virus SIVagm Infection", *J. Virol.*, 64, 6252–6256 (1990)). However, anti-CD4 antibodies are expected to prevent virus transmission independently of subtype and variability, but their application would be too costly (Daar et al, supra, Watanabe, M., Boyson, J. E., Lord, C. I. and Letvin, N. L. "Chimpanzees Immunized with Recombinant Soluble CD4 Develop Anti-self CD4 Antibody Responses with Anti-human Immunodeficiency Virus Activity", *Proc. Natl. Acad. Sci. U.S.A.*, 89, 5103–5107 (1992); and Perno, C. -F., Baseler, M. W., Broder, S. and Yarchoan, R., "Infection of Monocytes by Human Immunodeficiency Virus Type 1 Blocked by Inhibitors of CD4-gp120 Binding, Even in the Presence of Enhancing Antibodies", *J. Exp. Med.*, 171, 1043–1056 (1990)).

There is a need for a safe and effective substance that can be inserted into the vagina by a foam, gel, sponge or other form to prevent HIV-1 or HIV-2 from infecting cells in the body. It is hoped that such substance be used by a woman without her partner's knowledge.

Prospects for the near and possibly not so near future to prevent HIV-1 transmission by vaccination do not seem good. A recent report that vaccination with inactivated SIV did not protect African Green monkeys against infection with the homologous virus notwithstanding a strong immune response to SIV does not appear to be encouraging in this respect (Siegel, F., Kurth, R., and Norley, S., (1995), "Neither Whole Inactivated Virus Immunogen nor Passive Immunoglobulin Transfer Protects Against $SIV_{agm}$ Infection in the African Green Monkey Natural Host", *J. AIDS*, 8, 217–226). Considering this problem, emphasis has been put on attempts to build a chemical barrier to HIV-1 transmission (Taylor, (1994), "Building a Chemical Barrier to HIV-1 Transmission", *J. NIH Res.*, 6, 26–27).

The development of topically applied microbicides, expected to prevent sexual (mucosal) transmission of HIV-1, was suggested to need to be "effective against all sexually transmitted diseases and should not be seen, smelled, or felt while in use." It should also be inexpensive and widely available, and $25 million was expected to be devoted to its development in the United States in 1995 (Taylor,(1994) supra). Detergents (nonoxynol-9) as a universal pathogen killer have been selected for clinical trials. However, not surprisingly, this compound proved to be deleterious to the host.

Targeting the chemical barrier to transmission of individual pathogens could perhaps facilitate the development of compounds preventing the transmission of human immunodeficiency viruses. For example, effective blockade of receptors for the viruses might accomplish this goal. This concept may be supported by the finding that immunization of chimpanzees and rhesus monkeys, respectively, with human CD4 which has several amino acid point mutations in comparison with non-human primate CD4 sequences (Fomsgaard, A., Hirsch, V. M., and Johnson, P. R., (1992), "Cloning and Sequences of Primate CD4 molecules: Diversity of the Cellular Receptor for Simian Immunodeficiency Virus/Human Immunodeficiency Virus", *Eur. J. Immunol.*, 22, 2973–2981), developed anti-CD4 antibodies which inhibited HIV-1 and SIV replication (Watanabe, M., Levine, C. G., Shen, L., Fisher, R. A., and Letvin, N. L. (1991), "Immunization of Simian Immunodeficiency Virus-Infected Rhesus Monkeys with Soluble Human CD4 Elicits an Antiviral Response," *Proc. Natl. Acad. Sci. USA*, 88, 4616–4620. Watanabe, M., Chen, Z. W., Tsubota, H., Lord, C. I., Levine, C. G., and Letvin, N. L., (1991), "Soluble Human CD4 Elicits an Antibody Response in Rhesus-Monkeys that Inhibits Simian Immunodeficiency Virus Replication", *Proc. Natl. Acad. Sci. USA*, 88, 120–124; and Watanabe, M., Boyson, J. E., Lord, C. I., and Letvin, N. L., (1992), "Chimpanzees Immunized with Recombinant Soluble CD4 Develop Anti-self CD4 Antibody Responses with Anti-human Immunodeficiency Virus Activity", *Proc. Natl. Acad. Sci. USA*, 89, 5103–5107).

Herpesviruses include the following viruses isolated from humans:

(1) herpes simplex virus 1 ("HSV-1")
(2) herpes simplex virus 2 ("HSV-2")
(3) human cytomegalovirus ("HCMV")
(4) varicella-zoster virus ("VZV")
(5) Epstein-Barr virus ("EBV")
(6) human herpesvirus 6 ("HHV6")
(7) herpes simplex virus 7 ("HSV-7")
(8) herpes simplex virus 8 ("HSV-8")

Herpesviruses have also been isolated from horses, cattle, pigs (pseudorabies virus ("PSV") and porcine cytomegalovirus), chickens (infectious larygotracheitis), chimpanzees, birds (Marck's disease herpesvirus 1 and 2), turkeys and fish (see "Herpesviridae: A Brief Introduction", *Virology*, Second Edition, edited by B. N. Fields, Chapter 64, 1787 (1990)).

Herpes simplex viral ("HSV") infection is generally a recurrent viral infection characterized by the appearance on the skin or mucous membranes of single or multiple clusters of small vesicles, filled with clear fluid, on slightly raised inflammatory bases.

The herpes simplex virus is a relatively large-sized virus. HSV-2 commonly causes herpes labialis. HSV-2 is usually, though not always, recoverable from genital lesions. Ordinarily, HSV-2 is transmitted venereally.

The time of initial herpes simplex virus infection is usually obscure except in the uncommon primary systemic infection occurring in infants and is characterized by generalized cutaneous and mucous membrane lesions accompanied by severe constitutional symptoms. Localized infections ordinarily appear in childhood, but may be delayed until adult life. It is presumed that the herpes simplex virus remains dormant in the skin and that herpetic eruptions are precipitated by overexposure to sunlight, febrile illnesses, or physical or emotional stress; also, certain foods and drugs have been implicated. In many instances, the trigger mechanism remains undetected.

The lesions caused by herpes simplex virus may appear anywhere on the skin or on mucous membranes, but are most frequent on the face, especially around the mouth or on the lips, conjunctiva and cornea, or the genitals. The appearance of small tense vesicles on an erythematous base follows a short prodromal period of tingling discomfort or itching. Single clusters may vary from 0.5 to 1.5 cm in size, but several groups may coalesce. Herpes simplex on skin tensely attached to underlying structures (for example, the nose, ears or fingers) may be painful. The vesicles may persist for a few days, then begin to dry, forming a thin yellowish crust. Healing usually occurs within 10 days after onset. In moist body areas, healing may be slower, with secondary inflammation. Healing of individual herpetic lesions is usually complete, but recurrent lesions at the same site may result in atrophy and scarring.

In females infected with HSV-2, there may be no skin lesions, the infection may remain entirely within the vagina. The cervix is frequently involved, and there is increasing evidence that this may be a factor in the development of carcinoma of the cervix.

Corneal lesions commonly consist of a recurrent herpetic keratitis, manifest by an irregular dendritic ulcer on the superficial layers. Scarring and subsequent impairment of vision may follow.

Gingivostomatitis and vulvovaginitis may occur as a result of herpes infection in infants or young children. Symptoms include irritability, anorexia, fever, inflammation, and whitish plaques and ulcers of the mouth. Particularly in infants, though sometimes in older children, primary infections may cause extensive organ involvement and fatal viremia.

In women who have an attack of HSV-2 late in pregnancy, the infection may be transmitted to the fetus, with the development of severe viremia. Herpes simplex virus may also produce fatal encephalitis.

Kaposi's varicelliform eruption (eczema herpeticum) is a potentially fatal complication of infantile or adult atopic eczema. Exposure of patients with extensive atopic dermatitis to persons with active herpes simplex should be avoided.

No local or systemic chemotherapeutic agent has been demonstrated to be effective for treating herpes simplex virus with the possible exception of topical idoxuridine (IDU) in superficial herpetic keratitis. Reports on this compound in cutaneous herpes are conflicting. Other drugs which have been employed to treat HSV include trifluorothymidine, vidarabine (adenine arabinoside, ara-A), acyclovir, and other inhibitors of viral DNA synthesis may be effective in herpetic keratitis. These drugs inhibit herpes simplex virus replication and may suppress clinical manifestations. However, the herpes simplex virus remains latent in the sensory ganglia, and the rate of relapse is similar in drug-treated and untreated individuals. Moreover, some drug-resistant herpes virus strains have emerged.

Diseases caused by varicella-zoster virus (human herpesvirus 3) include varicella (chickenpox) and zoster (shingles).

Cytomegalovirus (human herpesvirus 5) is responsible for cytomegalic inclusion disease in infants. There is presently no specific treatment for treating patients infected with cytomegalovirus.

Epstein-Barr virus (human herpesvirus 4) is the causative agent of infectious mononucleosis and has been associated with Burkitt's lymphoma and nasopharyngeal carcinoma.

Animal herpesviruses which may pose a problem for humans include B virus (herpesvirus of Old World Monkeys) and Marmoset herpesvirus (herpesvirus of New World Monkeys).

In searching for inexpensive antiviral compounds which could be applied topically to decrease the frequency of sexual transmission of the human immunodeficiency virus type 1 (HIV-1) and herpesviruses (HSV), applicants decided against all odds to screen excipients for anti-HIV-1 activity and discovered the present invention which involves the administration of cellulose acetate phthalate ("CAP") or hydroxypropyl methylcellulose phthalate ("HPMCP").

SUMMARY OF THE INVENTION

An object of the present invention is to provide a safe and relatively inexpensive method to decrease the frequency of transmission of human immunodeficiency virus and herpesvirus viral infections, particularly those which are sexually transmitted.

A further object of the present invention is to provide a composition for decreasing the frequency of transmission of human immunodeficiency virus and herpesvirus.

The above objects are achieved by the present invention.

The present invention concerns a method for decreasing the frequency of transmission and, particularly, preventing the transmission of human immunodeficiency virus or herpesvirus by administering to a human an effective anti-human immunodeficiency virus or anti-herpesvirus amount of at least one cellulose phthalate selected from the group consisting of acetate phthalate (CAP) and hydroxypropyl methylcellulose phthalate (HPMCP) either alone, or in combination with a pharmaceutically acceptable carrier or diluent.

The present invention also concerns a pharmaceutical composition for decreasing the frequency of transmission of human immunodeficiency virus or herpesvirus comprising an effective anti-immunodeficiency virus amount or effective anti-herpesvirus amount of at least one cellulose phthalate selected from the group consisting of cellulose acetate phthalate and hydroxypropyl methylcellulose phthalate in combination with a pharmaceutically acceptable carrier or diluent.

The present invention is also directed to the aforesaid method and pharmaceutical composition, wherein the cellulose phthalate (CAP and/or HPMCP) is provided in the form of a suspension and preferably in a micronized form. Further, such suspension may include a water miscible, essentially anhydrous, non-solvent for CAP or HPMCP, such as glycerol.

BRIEF DESCRIPTION OF THE DRAWINGS

FIG. 1 thus shows the inhibitory effect of cellulose acetate phthalate ("CAP") on HSV-1 and HSV-2.

FIG. 3 shows the disintegration of purified HIV-1 by treatment with an "AQUATERIC"-glycerol formulation with or without polyvinyl pyrrolidone (PVP) and Crospovidone for 5 minutes at 37° C., as measured by the release of the nucleocapsid antigen p24.

FIG. 4 shows the inactivation of HIV-1 infectivity by treatment with an "AQUATERIC"-glycerol formulation containing 286 mg/ml of "AQUATERIC" for 5 minutes at 37° C., as determined by production of the nucleocapsid antigen p24 by infected cells as measured by ELISA.

FIG. 5 shows the inactivation of HSV-1 and HSV-2 by a suspension of "AQUATERIC" in glycerol. Virus preparations were mixed 1:1 with a suspension of "AQUATERIC" in glycerol for 5 minutes at 37° C.

FIG. 6 shows the inactivation of HSV-1 and HSV-2 by an "AQUATERIC"-glycerol formulation with PVP and Crospovidone.

DETAILED DESCRIPTION OF THE INVENTION

Figure 1:
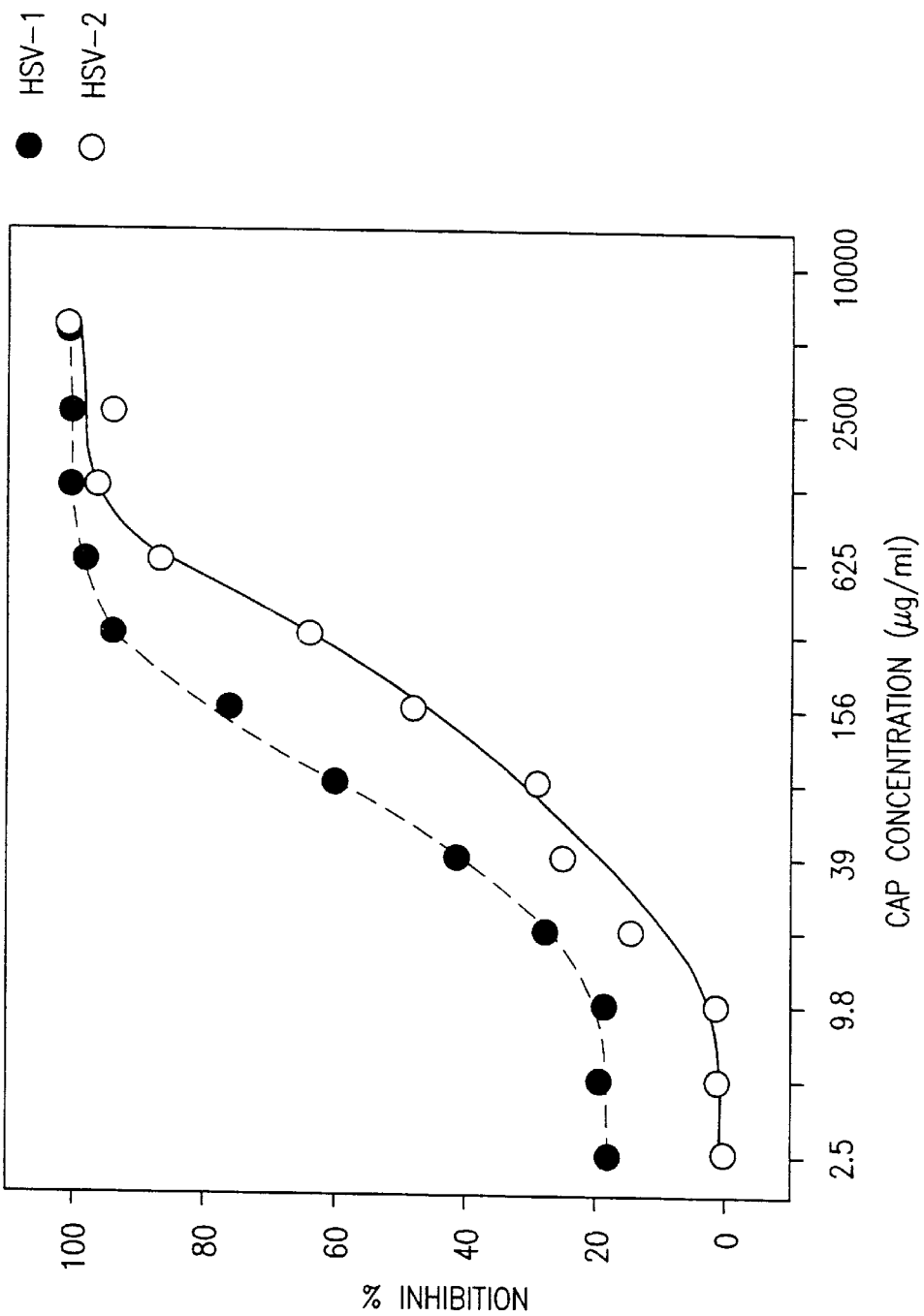
FIG. 1 is a graph of % inhibition vs. cellulose acetate phthalate ("CAP") concentration, for HSV-1 and HSV-2.

Some of the properties of CAP as described in the *Handbook of Pharmaceutical Excipients* are summarized as follows:

Non proprietary Names:
  BP: Cellacephate
  PhEur: Cellulosi acetas phthalas
  USPNF: Cellulose acetate phthalate Synonyms:
  Acetyl phthalyl cellulose; CAP; cellacefate; cellulose acetate hydrogen 1,2-benzenedicarboxylate; cellulose acetate hydrogen phthalate; cellulose acetate monophthalate; cellulose acetophthalate; cellulose acetylphthalate.

Chemical Name and CAS Registry Number:
  Cellulose, acetate, 1,2-benzenedicarboxylate [9004-38-0]
  Cellulose acetate phthalate is a cellulose in which about half the hydroxyl groups are acetylated and about a quarter are esterified, with one of the two acid groups being phthalic acid. The other acid group is free. See the structural formula below.

Structural Formula:

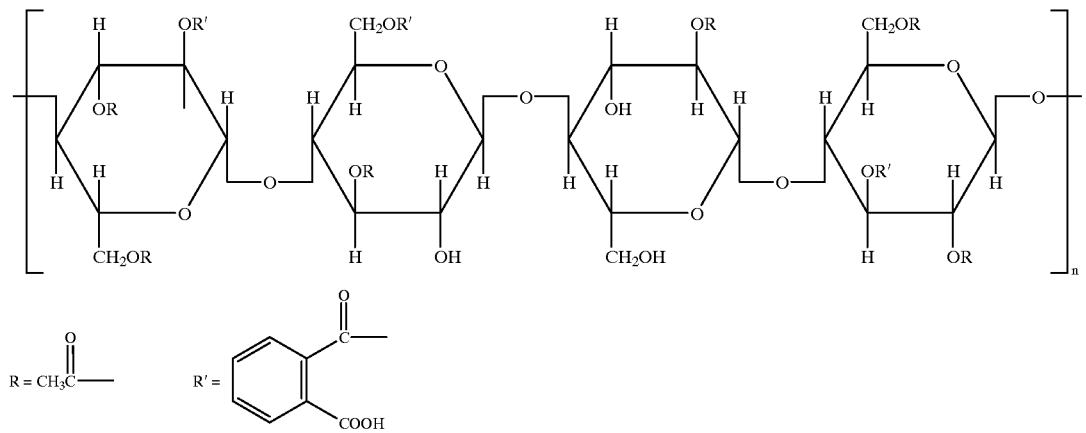

Functional Category:
  Coating agent.

Applications in Pharmaceutical Formulation or Technology:
  Cellulose acetate phthalate has heretofore been used as an enteric film coating material, or as a matrix binder, for tablets and capsules (Spitael, J., Kinget, R., Naessens, K., "Dissolution Rate of Cellulose Acetate Phthalate and Bronsted Catalysis Law", *Pharm. Ind.*, (1980), 42:846–849; Takenaka, H., Kawashima, Y., Lin, S -Y., "Preparation of Enteric-Coated Microcapsules for Tableting by Spray-Drying Technique and in vitro Simulation of Drug Release from the Tablet in GI Tract", *J. Pharm., Sci.*, (1980), 69:1388–1392; Stricker, H., Kulke, H., "Rate of Disintegration and Passage of Enteric-Coated Tablets in Gastrointestinal Tract", *Pharm. Ind.*, (1981), 43:1018–1021; Takenaka, H., Kawashima, Y., Lin, S -Y, "Polymorphism of Spray-Dried Microencapsulated Sulfamethoxazole with Cellulose Acetate Phthalate and Colloidal Silica Montmorillonite, or Talc", *J. Pharm. Sci.*, (1981), 70:1256–1260; Maharaj, I.; Nairn, J. G., Campbell J. B., "Simple Rapid method for the Preparation of Enteric-Coated Microspheres", *J. Pharm.*

*Sci.*, (1984), 73:39–42; Beyger, J. W., Nairn, J. G., "Some Factors Affecting the Microencapsulation of Pharmaceuticals with Cellulose Acetate Phthalate", *J. Pharm. Sci.*, (1986), 75-573–578; Lin, S -Y, Kawashima, Y., "Drug Release from Tablets Containing Cellulose Acetate Phthalate as an Additive or Enteric-Coating Material", *Pharm. Res.*, (1987), 4:70–74; Thoma, K. Hekenmüller, H., "Effect of Film Formers and Plasticizers on Stability of Resistance and Disintegration Behaviour, Part 4: Pharmaceutical-Technological and Analytical Studies of Gastric Juice Resistant Commercial Preparations", *Pharmazie*, (1987), 42:837–841).

Such coatings resist prolonged contact with the strongly acidic gastric fluid, but soften and swell in the mildly acidic or neutral intestinal environment.

Cellulose acetate phthalate, when heretofore used as an adjuvant, was commonly applied to solid dosage forms either by coating from organic or aqueous solvent systems, or by direct compression. Concentrations used were 0.5 to 9.0% of the core weight. The addition of plasticizers improves the water resistance of this coating material, and such plasticized films are more effective than when cellulose acetate phthalate is used alone as an adjuvant. Cellulose acetate phthalate is compatible with the following plasticizers: acetylated monoglyceride; butyl phthalylbutyl glycolate; dibutyl tartrate; diethyl phthalate; dimethyl phthalate; ethyl phthalyethyl glycolate; glycerin; propylene glycol; triacetin; triacetin citrate and tripropionin. Cellulose acetate phthalate has also been used heretofore in combination with other coating agents to control drug release, e.g., ethylcellulose.

Description:

Cellulose acetate phthalate is a hygroscopic, white, free-flowing powder or colorless flakes. It is tasteless and odorless, or may have a slight odor of acetic acid.

Pharmacopeial Specifications:

| Test | PhEur 1984 | USPNF XVII (Suppl 2) |
| --- | --- | --- |
| Identification | + | + |
| Appearance of solution | + | – |
| Appearance of a film | + | – |
| Solubility of a film | + | – |
| Viscosity at 25° C. | – | 45–90 cP |
| Water | ≦5.0% | ≦5.0% |
| Residue on ignition | – | ≦0.1% |
| Sulfated ash | ≦0.1% | – |
| Free acid | ≦3.0% | ≦6.0% |
| Heavy metals | ≦10 ppm | – |
| Phthalyl content | 30.0–40.0% | 30.0–36.0% |
| Acetyl content | 17.0–26.0% | 21.5–26.0% |

Typical Properties:

Hygroscopicity: cellulose acetate phthalate is hygroscopic and precautions are necessary to avoid excessive absorption of moisture (Callahan, J. C., Cleary, G. W., Elefant, M., Kaplan, G., Kensler, T., Nash, R. A., "Equilibrium Moisture Content of Pharmaceutical Excipients", *Drug Dev. Ind. Pharm.*, (1982), 8:355–369).

Melting point: 192° C. Glass transition temperature is 160–170° C. (Sakellariou, P., Rowe, R. C., White, E. F. T., "The Thermomechanical Properties and Glass Transition Temperatures of Some Cellulose Derivatives used in Film Coating", *Int. J. Pharmaceutics*, (1985), 27:267–277).

Solubility: practically insoluble in alcohols, chlorinated hydrocarbons, hydrocarbons, and water; soluble in cyclic ethers, esters, ether alcohols, ketones and certain solvent mixtures. Also soluble in certain buffered aqueous solutions at greater than pH 6. The following list shows some of the solvents and solvent mixtures in which cellulose acetate phthalate has a solubility of 1 in 10 parts or more.

Acetone
Acetone: Ethanol (1:1)
Acetone: Methanol (1:1/1:3)
Acetone: Methylene chloride (1:1/1:3)
Acetone: Water (97:3)
Benzene: Methanol (1:1)
Diacetone alcohol
Dioxane
Ethoxyethyl acetate
Ethyl acetate: Ethanol (1:1)
Ethyl acetate: Propan-2-ol (1:1/1:3)
Ethylene glycol monoacetate
Ethyl lactate
Methoxyethyl acetate
Methoxyethylene alcohol
Methyl acetate
Methylene chloride: Ethanol (3:1)
Methyl ethyl ketone Viscosity (dynamic): 50–90 mPas (50–90 cP) for a 15% w/w solution in acetone with a moisture content of 0.4%. This is a good coating solution with a honey-like consistency, but the viscosity is influenced by the purity of the solvent.

Stability and Storage Conditions:

Cellulose acetate phthalate hydrolyzes slowly under prolonged adverse conditions, such as high temperature and humidity, with a resultant increase in free acid content, viscosity and odor of acetic acid. If its moisture content is above about 6% w/w, fairly rapid hydrolysis occurs. However, cellulose acetate phthalate is stable if stored in a well-closed container in a cool, dry place.

Incompatibilities:

Cellulose acetate phthalate is incompatible with ferrous sulfate, ferric chloride, silver nitrate, sodium citrate, aluminum sulfate calcium chloride, mercuric chloride, barium nitrate, basic lead acetate, and strong oxidizing agents such as strong alkalis and acids. It should be noted that one carboxylic acid group of the phthalic acid moiety remains unesterified and free for interactions. Accordingly, incompatibility with acid sensitive drugs may occur (Rawlins E. A., editor, "Bentley's Textbook of Pharmaceutics", London: Baillière, Tindall and Cox, (1977), 291).

Method of Manufacture:

Cellulose acetate phthalate is produced by reacting the partial acetate ester of cellulose with phthalic anhydride in the presence of a tertiary organic base, such as pyridine.

Safety:

Cellulose acetate phthalate is widely used in oral pharmaceutical products and is generally regarded as a nontoxic material, free of adverse effects.

Results of long-term feeding studies with cellulose acetate phthalate, in rats and dogs, have indicated a low oral toxicity. Rats survived daily feedings of up to 30% in the diet for up to one year without showing a depression in growth. Dogs fed 16 g daily in the diet for one year also remained normal (Hodge, H. C., "The Chronic Toxicity of Cellulose Acetate Phthate in Rats and Dogs", *J. Pharmacol.*, 80, 250–255, (1944)).

Regulatory Status:

Included in the FDA Inactive Ingredients Guide (oral capsules and tablets). Included in nonparenteral medicines licensed in the United Kingdom.

Pharmacopeias: Aust, Br, Braz, Cz, Eur, Fr, Ger, Gr, Hung, Ind, It, Jpn, Mex, Neth, Nord, Port, Swiss and USPNF.

Some of the properties of HPMCP, described in the *Handbook of Pharmaceutical Excipients* are summarized as follows:

Non proprietary Names: BP: Hypromellose phthalate; PhEur: Methylhydroxypropylcellulosi phthalas and USPNF: Hydroxypropyl methylcellulose phthalate.

Synonyms: Cellulose phthalate hydroxypropyl methyl ether; HPMCP; 2-hydroxypropyl methylcellulose phthalate; methylhydroxypropylcellulose phthalate;

Chemical Name and CAS Registry Number: Cellulose, hydrogen 1,2-benzenedicarboxylate, 2-hydroxypropyl methyl ether [9050-31-1]

Structural Formula:

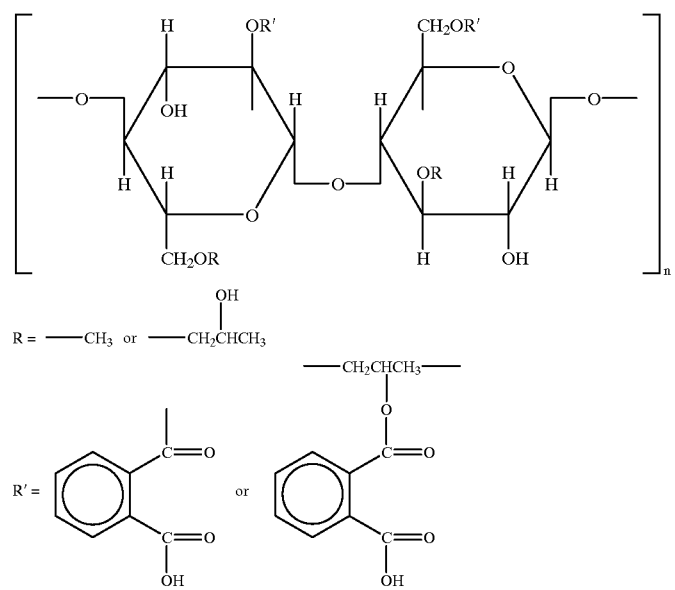

Functional Category: Coating agent.

Applications in Pharmaceutical Formulations or Technology

Hydroxypropyl methylcellulose phthalate has heretofore been widely used in oral pharmaceutical formulations as an enteric coating material for tablets or granules (Ehrhardt, L., Patt, L., Schindler, E., "Optimization of Film Coating Systems", *Pharm. Ind.*, (1973), 35:719–722; Delporte, J. P., Jaminet, F., "Influence of Formulation of Enteric-Coated Tablets on the Bioavailability of the Drug", *J. Pharm. Belq.*, (1976), 31-263–276; Patt, L., Hartmann V., "Solvent Residues in Film Forming Agents", *Pharm. Ind.*, (1976), 38:902–906; Stafford, J. W., "Enteric Film Coating Using Completely Aqueous Dissolved Hydroxypropyl Methylcellulose Phthalate Spray Solutions", *Druq. Dey Ind. Pharm.*, (1982), 8:513–530; Thoma, K., Heckenmuller, H., Oschmann, R., "Resistance and Disintegration Behaviour of Gastric Juice Resistant Drugs", *Pharmazie*, (1987), 42:832–836; Thoma, K., Heckenmuller, H., Oschmann, R., "Impact of Film Formers and Plasticizers on Stability of Resistance and Disintegration Behaviour", *Pharmazie*, (1987), 42:837–841).

Hydroxypropyl methylcellulose phthalate is insoluble in gastric fluid, but will swell and dissolve rapidly in the upper intestine. Generally, concentrations of 5–10% of hydroxypropyl methylcellulose phthalate were employed with the material being dissolved in either a dichloromethane:ethanol (50:50) or an ethanol:water (80:20) solvent mixture. Hydroxypropyl methylcellulose phthalate can normally be applied to tablets and granules without the addition of a plasticizer or other film formers, using established coating techniques (Rowe, R. C., "Molecular Weight Studies on the Hydroxypropyl Methylcellulose Phthalate (HP55)", *Acta. Pharm. Technol.*, (1982), 28(2):127–130. However, the addition of a small amount of plasticizer or water can avoid film cracking problems; many commonly used plasticizers such as diacetin, triacetin, diethyl and dibutyl phthalate, castor oil, acetyl monoglyceride and polyethylene glycols are compatible with hydroxypropyl methylcellulose phthalate. Tablets coated with hydroxypropyl methylcellulose phthalate disintegrate more rapidly than tablets coated with cellulose acetate phthalate.

Hydroxypropyl methylcellulose phthalate can be applied to tablet surfaces using a dispersion of the micronized hydroxypropyl methylcellulose phthalate powder in an aqueous dispersion of a suitable plasticizer such as triacetin, triethyl citrate or diethyl tartrate along with a wetting agent (Muhammad, N. A., Boisvert, W., Harris, M. R., Weiss, J., "Evaluation of Hydroxypropyl Methylcellulose Phthalate 50 as Film Forming Polymer from Aqueous Dispersion Systems", *Drug Dev. Ind. Pharm.*, (1992), 18:1787–1797).

Hydroxypropyl methylcellulose phthalate may be used alone or in combination with other soluble or insoluble binders in the preparation of granules with sustained drug release properties; the release rate is pH dependent. Since hydroxypropyl methylcellulose phthalate is tasteless and insoluble in saliva, it can be used as a coating to mask the unpleasant taste of some tablet formulations.

Description:

Hydroxypropyl methylcellulose phthalate occurs as white to slightly off-white colored free-flowing flakes or as a granular powder. It is odorless or with a slightly acidic odor, and a barely detectable taste.

Typical Properties:

Melting point: 150° C.

Solubility: practically insoluble in ethanol and water; very slightly soluble in acetone, and toluene; soluble in aqueous alkalis, a mixture of equal volumes of acetone and methanol, and in a mixture of equal volumes of dichloromethane and methanol.

Stability and Storage Conditions:

Hydroxypropyl methylcellulose phthalate is chemically and physically stable at ambient temperature and humidity for 3–4 years, and for 2 to 3 months at 40° C. and 75% relative humidity (Shin-Etsu Chemical Co., Ltd., Technical Literature: Hydroxypropyl Methylcelluose Phthalate, (1993). Hydroxypropyl methylcellulose phthalate is stable on exposure to UV light for up to 3 months at 25° C. and 70% relative humidity (Shin-Etsu Chemical Co., Ltd., Technical Literature : Hydroxypropyl Methylcelluose Phthalate, (1993). In general, hydroxypropyl methylcellulose phthalate is more stable than cellulose acetate phthalate. At ambient storage conditions, hydroxypropyl methylcellulose phthalate is not susceptible to microbial attack.

Incompatibilities:

Incompatible with strong oxidizing agents. Splitting of film coatings has been reported rarely, most notably with coated tablets which contain microcrystalline cellulose and calcium carboxymethylcellulose. Film splitting has also occurred when a mixture of acetone: propan-2-ol or dichloromethane: propan-2-ol has been used as a coating solvent, or when coatings have been applied in conditions of low temperature and humidity. However, film splitting may be avoided by careful selection of the coating solvent used, by using a higher molecular weight grade of polymer (Rowe, R. C., "Molecular Weight Studies on the Hydroxypropyl Methylcellulose Phthalate (HP55), *Acta. Pharm. Technol.*, (1982), 28(2):127–130), or by the addition of a plasticizer, such as acetyl monoglyceride or triacetin. The addition of more than about 10% titanium dioxide to a coating solution of hydroxypropyl methylcellulose phthalate, that is used to produce a colored film coating, may result in coatings with decreased elasticity and gastric fluid resistance (Shin-Etsu Chemical Co., Ltd., Technical Literature: Hydroxypropyl Methylcellulose Phthalate, (1993)).

Method of Manufacture:

Hydroxypropyl methylcellulose acetate phthalate is prepared by the esterification of hydroxypropyl methylcellulose with phthalic anhydride. The degree of methoxy and phthalyl substitution determines the properties of the polymer and in particular the pH at which it dissolves in aqueous media.

Safety:

Hydroxypropyl methylcellulose phthalate has been heretofore widely used, primarily as an enteric coating agent, in oral pharmaceutical formulations. Chronic and acute animal feeding studies on several different species have shown no evidence or teratogenicity or toxicity associated with hydroxypropyl methylcellulose phthalate (Kitagawa, H., Kawana, H., Satoh, T., Fukuda, Y., "Acute and Subacute Toxicities of Hydroxypropyl Methylcellulose Phthalate", *Pharmacometrics*, (1970), 4(6):1017–1025; Kitagawa, H., Satoh, T., Yokoshima, T., Nanbo, T., "Absorption, Distribution and Excretion of Hydroxypropyl Methylcellulose Phthalate in the Rat", *Pharmacometrics*, (1971), 5(1):1–4; Ito, R., Toida, S., "Studies on the Teratogenicity of a New Enteric Coating Material, Hydroxypropyl Methylcellulose Phthalate (HPMCP) in Rats and Mice", *J. Med. Soc. Toho-Univ.*, (1972), 19(5):453–461; Kitagawa, H., Yano, H., Fukuda, Y., "Chronic Toxicity of Hydroxypropylmethylcellulose Phthalate in Rats", *Pharmacometrics*, (1973), 7(5) ;689–701; Kitagawa, H., Yokoshima, T., Nanbo, T., Hasegawa, M., "Absorption, Distribution, Excretion and Metabolism of $^{14}$C-hydroxypropyl Methylcellulose Phthalate", *Pharmacometrics*, (1974), 8(8):1123–1132. Hydroxypropyl methylcellulose phthalate is generally regarded as a nonirritant and nontoxic material.

$LD_{50}$ (rat, oral):>15 g/kg (Kitagawa et al., *Pharmacometrics*, (1970), 4(6):1017–1025).

Regulatory Status: included in the FDA Inactive Ingredients Guide (oral capsules and tablets) and included in nonparenteral medicines licensed in the United Kingdom.

Pharmacopeias: Br, Eur, Fr, Gr, It, Jpn, Neth, Port, Swiss and USPNF.

Related Substances: cellulose acetate phthalate; Hydroxypropyl Methylcellulose.

A particularly preferred composition for topically administering to a human in accordance with the present invention comprises micronized CAP or micronized HPMCP, a poloxamer and distilled acetylated monoglycerides, suspended in glycerol (a mixture of micronized CAP, poloxamer and acetylated monoglycerides is sold by the FMC Corporation under the trade name "AQUATERIC".) A poloxamer is a nonionic polyoxyethylene-polyoxypropylene copolymer.

A chemical name for a poloxamer is α-hydro-ω-hydroxypoly(oxyethylene) poly(oxypropylene) poly (oxyethylene) block copolymer. The poloxamer polyols are a series of closely related block copolymers of ethylene oxide and propylene oxide conforming to the following formula:

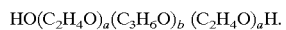

$HO(C_2H_4O)_a(C_3H_6O)_b(C_2H_4O)_aH.$

The following is a list of grades of poloxamers (USPNF XVII):

| Poloxamer | Physical Form | a | b | Average Molecular Weight |
|---|---|---|---|---|
| 124 | Liquid | 12 | 20 | 2,090 to 2,360 |
| 188 | Solid | 80 | 27 | 7,680 to 9,510 |
| 237 | Solid | 64 | 37 | 6,840 to 8,830 |
| 338 | Solid | 141 | 44 | 12,700 to 17,400 |
| 407 | Solid | 101 | 56 | 9,840 to 14,600 |

To prevent separation from the glycerol of the microsuspension containing the CAP or HPMCP, the poloxamer and the distilled acetylated monoglycerides, it is preferred to add PVP and a 1-ethenyl-2-pyrrolidinone homopolymer (Crospovidone) (Polyplasdone) $(C_6H_9NO)_n$, molecular weight >1,000,000) (water insoluble synthetic cross-linked homopolymer of N-vinyl-2-pyrrolidinone).

The term micronized used herein refers to particles having a particle size of less than 35 microns, preferably less than 15 microns, more preferably less than 10 microns and most preferably less than 5 microns.

In the composition described herein which includes glycerol, the glycerol may be replaced with a saline solution or water, so long as the composition is stored at ≦25° C.

A preferred composition for administration in the present invention can be made as follows: dissolve PVP in glycerol, then add 1-ethenyl-2-pyrrolidinone homopolymer (Crospovidone) and a composition comprising micronized CAP and poloxamer and acetylated monoglycerides. The PVP and 1-ethenyl-2-pyrrolidinone homopolymer would be in concentrations sufficient to stabilize the suspension of "AQUATERIC" in glycerol.

The method of the present invention can be used to prevent the transmission of human immunodeficiency virus, such as HIV-1 and HIV-2, and herpesvirus, in humans. The present invention is thus effective for preventing the transmission of HIV-1,or HSV, such as HSV-1, HSV-2, HSV-7 and HSV-8, as well as human cytomegalovirus, varicella-zoster virus, Epstein-Barr virus and human herpesvirus 6.

Preferred embodiments of the present invention are for preventing the transmission of HIV-1, HSV-1, or HSV-2, which are known to be transmitted sexually and HSV-8, which is known to be a causative agent of Kaposi's sarcoma.

In the methods of the present invention for preventing the transmission of HIV or herpesvirus infection in a human, a pharmaceutically effective anti-viral amount of CAP or HPMPC or both is administered to a human. It is preferred that the composition for use in the present invention be administered to an appropriate region of the human body.

The phrase "administration to an appropriate region of the body" includes, for example, application of the (active ingredient (CAP or HPMPC or both) or a composition containing the same used to regions of the body of a human, for example, the region of the human body which comes into close contact with another human body, for example, application (directly or indirectly) to the male or female genitalia to prevent transmission of HIV-1, HSV-1 and HSV-2 during sexual intercourse.

The term "local administration" includes any method of administration in which the activity of the CAP or HPMCP or both used in the present invention is substantially confined to the region of the human's body to which it is applied, i.e., vaginal or rectal (topical) administration.

The present invention is thus particularly effective for providing a method of preventing the transmission of HIV or herpesvirus infection which is transmitted by sexual contact, such as vaginal transmission, either during sexual intercourse or during childbirth (vaginal delivery), by vaginal administration, such as by administering a cream, ointment, lotion, jelly, solution, emulsion or foam formulation containing a pharmaceutically effective anti-HIV-1 or anti-HSV amount of CAP (such as micronized CAP) or HPMCP (such as micronized HPMCP) or both, either alone or in combination with a pharmaceutically acceptable carrier or diluent.

To prevent transmission of HIV-1 or herpesvirus infection which is transmitted by sexual contact, CAP or HPMCP (such as micronized CAP or HPMCP) or both can be applied to a contraceptive device (for example, a male or female condom, a contraceptive diaphragm or a contraceptive sponge, for example, a polyurethane foam sponge), prior to sexual intercourse.

Alternatively, CAP or HPMCP or both can be applied on a pessary or tampon for vaginal administration. The pharmaceutical formulation for topical administration would comprise a pharmaceutically effective anti-HIV or anti-herpesvirus amount of CAP or HPMCP or both and at least one pharmaceutically acceptable topical carrier or diluent, to form an ointment, cream, gel, lotion, paste, jelly, spray or foam.

The amount (dosage) of the active ingredient (CAP or HPMCP or both) in a topical formulation for use in the present invention will, in general, be less than 1,000 milligrams, preferably between 200 to 800 milligrams.

It is preferable to administer the active ingredient in conjunction with a pharmaceutically acceptable diluent or carrier, as a pharmaceutical formulation. The present invention thus also involves the use of a pharmaceutical formulation or composition comprising the active ingredient together with one or more pharmaceutically acceptable carriers or diluents and, optionally, other prophylactic ingredients. The carrier(s) or diluent(s) should be "acceptable" in the sense of being compatible with the other ingredients of the formulation and not deleterious to the recipient.

Pharmaceutical formulations include those suitable for vaginal, rectal or topical administration. The formulations may, where appropriate, be conveniently presented in discrete dosage units and may be prepared by any of the methods well known in the art of pharmacy. All such methods include the step of bringing into association the active ingredient with liquid carriers, gels or finely divided solid carriers or both and then, if necessary, shaping the product into the desired formulation.

Formulations suitable for vaginal administration may be presented as pessaries, tampons, creams, gels, pastes, jelly, foams or sprays or aqueous or oily suspensions, solutions or emulsions (liquid formulations) containing in addition to the active ingredient, such carriers as are known in the art to be appropriate. These formulations are useful to protect not only against sexual transmission of HIV or HSV, but also to prevent infection of a baby during passage through the birth canal. Thus the vaginal administration can take place prior to sexual intercourse, during sexual intercourse, and immediately prior to childbirth.

As a vaginal formulation, the active ingredient may be used in conjunction with a spermicide and as discussed above, may be employed with a condom, a diaphragm, a sponge or other contraceptive device.

Pharmaceutical formulations and preparations suitable for administration may conveniently be presented as a solution, an aqueous or oily suspension, or an emulsion. The active ingredient may also be presented as a bolus, electuary or paste.

Liquid preparations for vaginal administration may contain conventional additives such as suspending agents, emulsifying agents, non-aqueous vehicles (which may include edible oils) or preservatives.

Pharmaceutical formulations suitable for rectal or vaginal administration, wherein the carrier is a solid, are most preferably represented as unit dose suppositories. Suitable carriers include cocoa butter and other materials commonly used in the art, and the suppositories may be conveniently formed by admixture of the active compound with the softened or melted carrier(s) followed by chilling and shaping in molds.

Drops may be formulated with an aqueous or non-aqueous base comprising one or more dispersing agents, solubilizing agents or suspending agents. Liquid sprays are conveniently delivered from pressurized packs.

When desired, the above described formulations adapted to give sustained release of the active ingredient may be employed.

The pharmaceutical compositions for use according to the invention may also contain other active ingredients, such as spermicides, or antimicrobial agents, preservatives or other anti-viral agents.

Applicants discovered that two of many pharmaceutical excipients display a potent anti-HIV-1 activity effect. This is of enormous importance since excipients are inexpensive compounds. The expected dose of CAP or HPMCP per single topical application (approximately 300 mg) is expected to cost approximately 1.33 US cents. Thus, the application of CAP and/or HPMCP for decreasing the frequency of sexual transmission of HIV-1 is economically feasible worldwide and is expected to contribute to the control of the worldwide HIV-1 epidemic.

Figure 2:
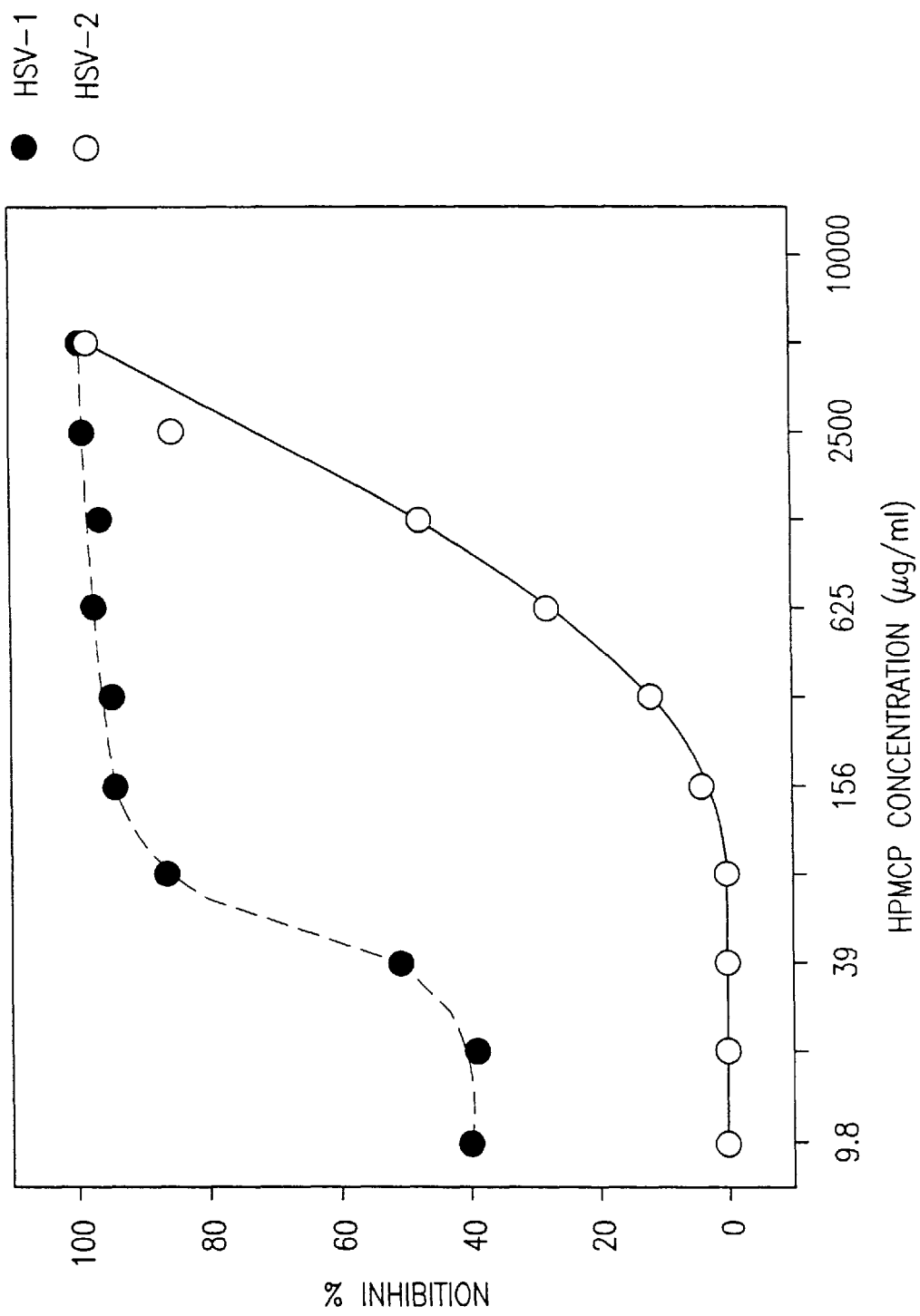
FIG. 2 is a graph of % inhibition vs. HPMCP concentration, for HSV-1 and HSV-2. The results shown in FIG. 2 are similar to those shown in FIG. 1.

Since viruses other than HIV-1 are also transmitted sexually, it was of interest to determine whether CAP and/or HPMCP may also inhibit infection by such viruses. Herpesvirus type 1 (HSV-1) and type 2 (HSV-2) were selected for these experiments. Results summarized in the figure indicate that CAP inhibited infection by both HSV-1 and HSV-2. Similar results were obtained with HPMCP (see FIG. 2).

EXAMPLES

Example 1

Screening Pharmaceutical Excipients for Anti-HIV Activity

The selection of pharmaceutical excipients to screen for anti-HIV activity was made from a list of pharmaceutical excipients derived from the *Handbook of Pharmaceutical Excipients*, edited by Ainley Wade and Paul J. Weller, 2$^{nd}$ edition, American Pharmaceutical Association, Washington, D.C. and the Pharmaceutical Press, London, (1994). The selected compounds are listed in the following Table 1A. Other excipients listed in the *Handbook of Pharmaceutical Excipients* were not tested for anti-HIV-1 activity, since it was known from earlier studies that they do not have such activity (see the following Table 2). Compounds insoluble in water or buffers (see the following Table 3), organic compounds including oils, waxes, solvents and detergents known to solubilize cell membranes and envelopes of lipid-containing viruses (see the following Table 4), gases used for aerosol propellants (see the following Table 5), and oxidizing agents and disinfectants with antibacterial activity (see the following Table 6) were excluded from the screening process.

Surprisingly, of all the compounds listed in Table 1A, only two compounds inhibited fusion between HIV-1 infected and uninfected cells, corresponding to a method for rapidly assessing the anti-HIV-1 activity of compounds. In this assay, HIV-1 IIIB infected H9 cells were labeled by 2',7'-bis-(2-carboxyethyl)-5-(and-6)-carboxyfluorescein acetoxymethyl ester (BCECF; Molecular Probes, Inc., Eugene, Oreg.) according to the manufacturer's instructions. BCECF-labeled H9/HIV-1 IIIB cells ($10^4$) were mixed with $2 \times 10^5$ uninfected MT-2 cells. After incubation in a 96-well plate at 37° C for 1 hour, the fused and unfused labeled cells were counted under an inverted fluorescence microscope at a 160× magnification. At least 200 BCECF-labeled cells were counted and the proportion of fused cells was determined. All experiments with HIV-1 were carried out under P2 biohazard containment levels.

The anti-HIV-1 activity of the two compounds, namely cellulose acetate phthalate and hydroxypropyl methylcellulose phthalate, listed in Table 1 was confirmed and quantitated by the following additional tests: inhibition of the cytopathic effect (CPE) of HIV-1 and inhibition of production of the HIV-1 nucleocapsid antigen (p24) (Table 1B). The two compounds were not toxic for uninfected cells at concentrations s 2,500 μg/ml.

$10^4$ MT-2 cells in 96-well plates were infected with HIV-1 (a dose sufficient to accomplish a multiplicity of infection of 0.0045) in 200 μl of RPMI 1640 medium supplemented with 10 vol. % fetal bovine serum. After 1 hour and 24 hours, half of the culture medium was changed and replaced by fresh medium. On the fourth day after incubation at 37° C., 100 μl of culture supernatants were collected from each well and an equal volume of fresh medium was added to the wells. The collected supernatants were mixed with an equal volume of 5 vol. % TRITON X-100 and assayed for the P24 antigen using an ELISA (Enzyme-linked immunoassay) kit from Coulter Immunology (Hialeah, Fla.). On the sixth day after infection, an indicator, XTT Tetrazolium Dye (1 mg/ml; 50 μl/well; PolySciences, Inc., Warrington, Pa.) was added to the cells. After 4 hours, intracellular formazan was determined colorometrically at 450 nm following the described procedure (Weislow O. S. et al., "New Soluble-Formazan Assay for HIV-1 Cytopathic Effects: Application to High-Flux Screening of Synthetic and Natural Products for AIDS-Antiviral Activity", *J. Natl. Cancer Inst.*, 81:577–586, (1989)). The percentage of cytopathogenesis was calculated using the following formula: 100×[($OD_{450}$ in negative control–$OD_{450}$ in experiment)/($OD_{450}$ in negative control–$OD_{450}$ in positive control)]. The negative control corresponded to cells mixed with culture medium, instead of HIV-1, while the positive control represented cells mixed with 100 $TCID_{50}$ (tissue culture infectious doses) of HIV-1 IIIB, which lysed 100% of the MT-2 cells. The cytopathic effect of the compounds on uninfected cells was measured using the same methodology.

TABLE 1A

Pharmaceutical Excipients Tested for Anti-HIV-1 Activity

| COMPOUND | Inhibition of Cell Fusion $*ED_{50} \pm SD$ (μg/ml) |
|---|---|
| Acacia | —** |
| Acesulfame Potassium | — |
| Alginic Acid | — |
| Ascorbyl Palmitate | — |
| Aspartame | — |
| Benzyl Benzoate | — |
| Bronopol | — |
| Butylated Hydroxyanisole | — |
| Butylated Hydroxytoluene | — |
| Butylparaben | — |
| Carbomer 934P | — |
| Carboxymethylcellulose | — |
| Cellulose Acetate Phthalate | 51.91 ± 1.32 |
| Chlorocresol | — |
| Croscarmellose Sodium | — |
| Dextrates | — |
| Dibutyl Sebacate | — |
| Ethylparaben | — |
| Hydroxyethyl Cellulose | — |
| Hydroxypropyl Cellulose | — |
| Hydroxypropyl Methylcellulose | — |
| Hydroxypropyl Methylcellulose Phthalate | 68.30 ± 11.48 |
| Imidurea | — |
| Maltodextrin | — |
| Maltol | — |
| Menthol | — |
| Methylcellulose | — |
| Methylparaben | — |
| Poloxamer | — |
| Polymethacrylates | — |
| Povidone | — |
| Propyl Gallate | — |
| Propylene Carbonate | — |
| Propylene Glycol | — |
| Alginate | — |
| Propylparaben | — |
| Saccharin | — |
| Sodium Alginate | — |
| Sodium Cyclamate | — |
| Sodium Starch Glycolate | — |
| Sodium Stearyl Fumarate | — |
| Sorbic Acid | — |
| Pregelatinized Starch | — |
| Triacetin | — |
| Vanillin | — |
| Vinylacetate Phthalate | — |
| Xanthan Gum | — |

$*ED_{50}$ = Effective dose for 50% inhibition of HIV-1 induced cell fusion.
**— = means no inhibitory activity on HIV-1 induced cell fusion at the final concentration of 1000 μg/ml.

TABLE 1B

Pharmaceutical Excipients Tested for Anti-HIV-1 Activity

| Inhibition of HIV-1 Infection | Cellulose Acetate Phthalate | | Hydroxypropyl Methylcellulose Phthalate | |
|---|---|---|---|---|
| | $ED_{50}^* \pm SD$ ($\mu$g/ml) | $ED_{90}^* \pm SD$ ($\mu$g/ml) | $ED_{50}^* \pm SD$ ($\mu$g/ml) | $ED_{90}^* \pm SD$ ($\mu$g/ml) |
| p24 Production | 2.54 ± 0.16 | 4.76 ± 1.05 | 4.76 ± 1.20 | 8.86 ± 1.11 |
| CPE | 3.68 ± 0.74 | 7.62 ± 1.66 | 7.79 ± 1.30 | 15.62 ± 7.61 |
| Cell Fusion | 51.91 ± 1.32 | 94.89 ± 3.12 | 68.30 ± 11.48 | 157.32 ± 32.86 |

*$ED_{50(90)}$ = Effective dose(s) for 50% (90%) inhibition of HIV-1 mediated p24 production, CPE and cell fusion.

TABLE 2

Compounds Known Not to Have Anti-HIV-1 Activity

| | |
|---|---|
| Albumin | Meglumine |
| Alpha Tocopherol | Monoethanolamine |
| Ascorbic Acid | Polyethylene Glycol |
| Benzoic Acid | Polyvinyl Alcohol |
| Benzyl Alcohol | Potassium Chloride |
| Dibasic Calcium Phosphate | Potassium Citrate |
| Calcium Sulfate | Potassium Sorbate |
| Cholesterol | Propylene Glycol |
| Citric Acid Monohydrate | Sodium Bicarbonate |
| Cyclodextrins | Sodium Chloride |
| Dextrin | Sodium Citrate Dihydrate |
| Dextrose | Sodium Metabisulfite |
| Diethanolamine | Dibasic Sodium |
| Diethyl Phthalate | Monobasic Sodium |
| Edetic Acid | Sodium Propionate |
| Ethyl Maltol | Sorbitol |
| Ethyl Vanillin | Starch |
| Fructose | Sterilizable Maize Starch |
| Fumaric Acid | Sucrose |
| Gelatin | Compressible Sugar |
| Liquid Glucose | Confectioner's Sugar |
| Glycerin | Sugar Spheres |
| Guar Gum | Tartaric Acid |
| Lactic Acid | Thimerosal |
| Lactose | Triethanolamine |
| Malic Acid | Triethyl Citrate |
| Maltitol Solution | Xylitol |
| Mannitol | |

TABLE 3

Compounds Insoluble in Water or Buffers

| | |
|---|---|
| Bentonite | Magnesium Carbonate |
| Calcium Carbonate | Magnesium Oxide |
| Calcium Stearate | Magnesium Stearate |
| Carboxymethylcellulose Calcium | Magnesium Trisilicate |
| Microcrystalline Cellulose | Polacrilin Potassium |
| Powdered Cellulose | Shellac |
| Cetostearyl Alcohol | Colloidal Silicon Dioxide |
| Cetyl Alcohol | Suppository Bases |
| Cetyl Esters Wax | Talc |
| Crospovidone | Titanium Dioxide |
| Ethylcellulose | Tragacanth |
| Kaolin | Zein |
| Magnesium Aluminum Silicate | Zinc Stearate |

TABLE 4

Organic Compounds, Oils, Waxes and Solvents and Detergents Solubilizing Cell Membranes and Envelopes of Lipid Containing Viruses

| | |
|---|---|
| Alcohol | Paraffin |
| Benzalkonium Chloride | Peanut Oil |
| Benzethonium Chloride | Petrolatum |
| Canola Oil | Petrolatum and Lanolin |
| Hydrogenated Castor Oil | Alcohols |
| Cetrimide | Polyoxyethylene Alkyl Ethers |
| Corn Oil | Polyoxyethylene Castor Oil |
| Cottonseed Oil | Derivatives |
| Docusate Sodium | Polyoxyethylene Sorbitan |
| Ethyl Oleate | Fatty Acid Esters |
| Glyceryl Monooleate | Polyoxyethylene Stearates |
| Glyceryl Monostearate | Sesame Oil |
| Glyceryl Palmitostearate | Sodium Lauryl Sulfate |
| Glycofurol | Sorbitan Esters (Sorbitan |
| Isopropyl Alcohol | Fatty Acid Esters) |
| Isopropyl Myristate | Soybean Oil |
| Isopropyl Palmitate | Stearic Acid |
| Lanolin | Stearyl Alcohol |
| Lanolin Alcohols | Hydrogenated Vegetable Oil |
| Hydrous Lanolin | Type 1 |
| Lecithin | Anionic Emulsifying Wax |
| Medium Chain Triglycerides | Carnauba Wax |
| Mineral Oil | Microcrystalline Wax |
| Light Mineral Oil | Nonionic Emulsifying Wax |
| Mineral Oil and Lanolin | White Wax |
| Alcohols | Yellow Wax |
| Oleic Acid | |

TABLE 5

Gases Used for Example in Aerosol Propellants

| | |
|---|---|
| Butane | Dimethyl Ether |
| Carbon Dioxide | Isobutane |
| Chlorodifluoroethane | Nitrogen |
| Chlorodifluoromethane | Nitrous Oxide |
| Dichlorodifluoromethane | Propane |
| Dichlorotetrafluoroethane | Tetrafluoroethane |
| Difluoroethane | Trichloromonofluoromethane |

TABLE 6

Oxidizing Agents and Disinfectants

| | | |
|---|---|---|
| Chlorhexidine | Phenol | Phenylmercuric Acetate |
| Chlorobutanol | Phenoxyethanol | Phenylmercuric Borate |
| Cresol | Phenylethyl Alcohol | Phenylmercuric Nitrate |

Example 2

Measurement of Inhibitory Ability Against HSV-1 and HSV-2

The following method was used to measure the inhibitory activity: 500 $\mu$l of compounds (at distinct dosages) in Eagle's Minimum Essential Medium (EMEM) were mixed with an equal volume of appropriately diluted infectious HSV-1 or HSV-2. The mixture was added to ELVIS HSV cells in 24-well plates. The ELVIS cells as well as the media were provided by Diagnostic Hybrids, Inc. (Athens, Ohio).

ELVIS cells are derived by selection of G418-resistant colonies following cotransfection of baby hamster kidney cells with a plasmid which contains a G418-antibiotic-resistant marker and a plasmid which contains an *Escherichia coli* LacZ gene placed behind an inducible HSV promoter. The promoter is from HSV-1UL39 which encodes ICP6, the large subunit of ribonucleotide reductase (RR1). This promoter has a number of features which make it ideal for the detection of HSV. First, there is no constitutive expression from this promoter in uninfected cells. Second, activation of the promoter appears to be specific for HSV. Third, expression from this promoter occurs within hours after infection. Fourth, this promoter is strongly transactivated by the virion associated trans-activator protein VP16. As early as six hours after infection, HSV-infected cells can be detected by histochemical staining for β-galactosidase activity (Stabell E. C. and Olivo P. D., "Isolation of a Cell Line for Rapid and Sensitive Histochemical Assay for the Detection of Herpes Simplex Virus", *J. Virological Methods*, 38:195–204, (1992)).

Twenty four hours after HSV infection, in the presence and absence of graded quantities of the test compounds, the ELVIS cells were lysed with TRITON X-100 and β-galactosidase in the cell lysates was determined by an ELISA kit provided by Five Prime→Three Prime, Inc. (Boulder, Colo.). This ELISA kit is capable of detecting and quantitating picogram levels of *E. coli* β-galactosidase protein expressed in transformed bacteria or eukaryotic cells and tissues. The method is based on detection of the β-galactosidase protein rather than on the enzymatic activity. β-galactosidase from *E. coli* is a tetrameric enzyme composed of four identical subunits. The individual subunits do not exhibit enzyme activity and therefore are not detectable by standard enzyme activity assays. The Five Prime→Three Prime β-galactosidase ELISA kit overcomes this limitation by detecting the actual protein that is expressed.

The surprising conclusion of the described experiments was that cellulose acetate phthalate and hydroxypropyl methylcellulose phthalate, of all the excipients tested, were unique in having potent antiviral activity against both HIV-1 and HSV-1 and HSV-2, and against other viruses belonging to the herpesvirus group.

Example 3

Formulations of CAP

The formulation of CAP and HPMCP for topical vaginal application as an antiviral agent or virucide to prevent the sexual transmission of HIV-1 and herpesviruses, respectively, represented a difficult challenge which could be overcome only by innovative approaches. Both CAP and HPMCP are insoluble in water and can be solubilized in water by adjusting the pH of the environment to ≈6 or above (*Handbook of Pharmaceutical Excipients*, 2nd Edition, edited by Ainley Wade and Paul J. Weller, American Pharmaceutical Association, Washington, (1994)), or by the use of appropriate organic solvents. On the other hand, vaginal secretions from healthy, reproductive-age women are characteristically acidic (pH values of 3.4 to 6.0) (B. Voeller, D. J. Anderson, "Heterosexual Transmission of HIV", *JAMA*, 267, 1917–1918, (1992)) Consequently, the topical application of a formulation in which either CAP or HPMCP would be soluble (i.e., pH=≧6) would be expected to contribute to a vaginal environment which is physiologically undesirable. Nevertheless, attempts were made to formulate CAP or HPMCP in gels/creams which are customarily used for vaginal applications as moisturizers and/or contraceptive agents. These included the following:
hydroxyethylcellulose gels (e.g., K-Y JELLY, Johnson and Johnson, Raritan, N.J.); carbomer 934P based gels (e.g., REPLENS, Roberts Pharmaceuticals, Inc., Mississauga, Ontario, Canada; Taro gel, Taro Pharmaceuticals, Inc., Bramalea, Ontario, Canada); hydroxypropyl methylcellulose and carbomer 934P based gels (e.g., H-R lubricating jelly, Carter-Wallace, Inc., New York, N.Y.); polyglyceryl methacrylate (Gyne-Moistrin Moisturizing Gel (Shering-Plough Healthcare Products, Inc., Mississauga, Ontario, Canada)), and gels containing carbomer 934P and hydroxypropyl methylcellulose alone. All the aforementioned formulations have water as their major constituent. When the preparations of CAP and HPMCP in the above gels were submitted to accelerated stability studies for 7 days at 45° C. and subsequently tested for anti-HIV-1 activity, no antiviral activity was detected. This was probably due to the hydrolysis of each of these cellulose derivatives, resulting in the release of acetic and phthalic acids and leading to diminished anti-HIV-1 activity.

To avoid this problem, it was decided to dissolve the cellulose derivatives (experiments were carried out mostly with CAP which has higher anti-HIV-1 activity in comparison with HPMCP; see Table 1B herein) in organic solvents that are low in water content, yet water miscible for in vivo compatibility, and nontoxic to vaginal mucosa, selected on the basis of preliminary studies. These solvents included the following: propylene glycol, propylene carbonate, benzyl alcohol, polyethylene glycol (PEG 400), dimethyl isosorbide, and ethoxydiglycol ("TRANSCUTOL"). The solubility of CAP in these solvents ranges between 5.3 to 30% (w/w). To increase the viscosity of these solutions, it was necessary to use them as gels/creams for topical applications. Either polyvinyl pyrrolidone (PVP) and/or different poloxamers (e.g., Pluronic F68) were added to the CAP solutions in the different organic solvents. To estimate the properties of the different formulations after contact with a physiological environment, they were mixed with water or physiological saline (0.14M NaCl). Under these conditions, CAP precipitated at the interface of the formulations with water (saline) in the form of a large polymeric mass which would not be expected to have antiviral activity and would not be appropriate for topical application. It was possible to overcome this problem by incorporating into the CAP containing formulation compounds which increase the pH upon contact with water or a saline solution (=0.14M NaCl), e.g., sodium acetate or triethanolamine. Inclusion of the latter compounds into the formulation eliminated or diminished the problem of appearance of large CAP aggregates. Surprisingly, accelerated stability studies (incubation for 7 days at 45° C.) of CAP in the above organic pharmaceutical excipients/solvents, containing in addition the aforementioned gelling and buffering agents, resulted in complete loss of anti-HIV-1 activity. This activity was retained if the buffering agents were omitted and added only before initiating the assay for anti-HIV-1 activity. Thus, in summary, the CAP formulations in organic solvents containing also a buffering agent represent formulations unsuitable for topical applications, either because the active ingredient, CAP, precipitates from the formulation in a large polymeric mass upon contact with physiological fluids (in the absence of appropriate buffering agents incorporated into the formulation) or are converted into useless formulations lacking anti-HIV-1 activity, because of inactivation of the active ingredient, CAP (in the absence of buffering agents).

To avoid the above problems, the possibility of using CAP in the form of a micronized preparation in suspension was explored. This necessitated the use of a solvent in which CAP would not be soluble, since otherwise the results obtained would be expected to be exactly the same as were those referred to above. A solvent with such properties is actually water in which neither CAP nor HPMCP are soluble (*Handbook of Pharmaceutical Excipients,* 2nd Edition, edited by Ainley Wade and Paul J. Weller, American Pharmaceutical Association, Washington (1994)).

A formulation containing water and a commercially available micronized form of CAP ("AQUATERIC" from the FMC Corporation, Philadelphia, Pa.), containing in addition to CAP (63 to 70 wt %), poloxamer and distilled acetylated monoglycerides, was prepared. Thickening agents, i.e., PVP and/or pluronic F68, were added to the water suspension of the "AQUATERIC". When this gel was submitted to accelerated stability studies (7 days at 45° C.) and then tested for anti-HIV-1 activity, essentially no antiviral activity was recovered. Thus, another solvent was needed in which the CAP ("AQUATERIC") would not be soluble and would not lose antiviral activity. Surprisingly, glycerol (very similar to propylene glycol in which CAP is soluble to ≈30% w/w) meets both these requirements. Based on this discovery, a formulation of CAP ("AQUATERIC") was prepared as follows: 200 mg of PVP (MW 40,000, Spectrum) were dissolved in 1 ml of glycerol. Subsequently, 50 mg of Crospovidone (Polyplasdone INF-10, ISP Technologies) were suspended in the solution followed by the addition of 286 mg of "AQUATERIC". The PVP and Crospovidone were added to prevent the separation of the "AQUATERIC" microsuspension from glycerol. The resulting formulation maintained its uniformity over time and also its anti-HIV-1 activity following an accelerated stability test carried out under conditions described above. Both the anti-HIV-1 activity and the anti-HSV-1 and anti-HSV-2 activities of this formulation, before or after stability testing, corresponded to the content of CAP in the preparation and to results shown in Table 1B and FIGS. 1 and 2 for HIV-1 and herpesviruses, respectively.

Figure 3:
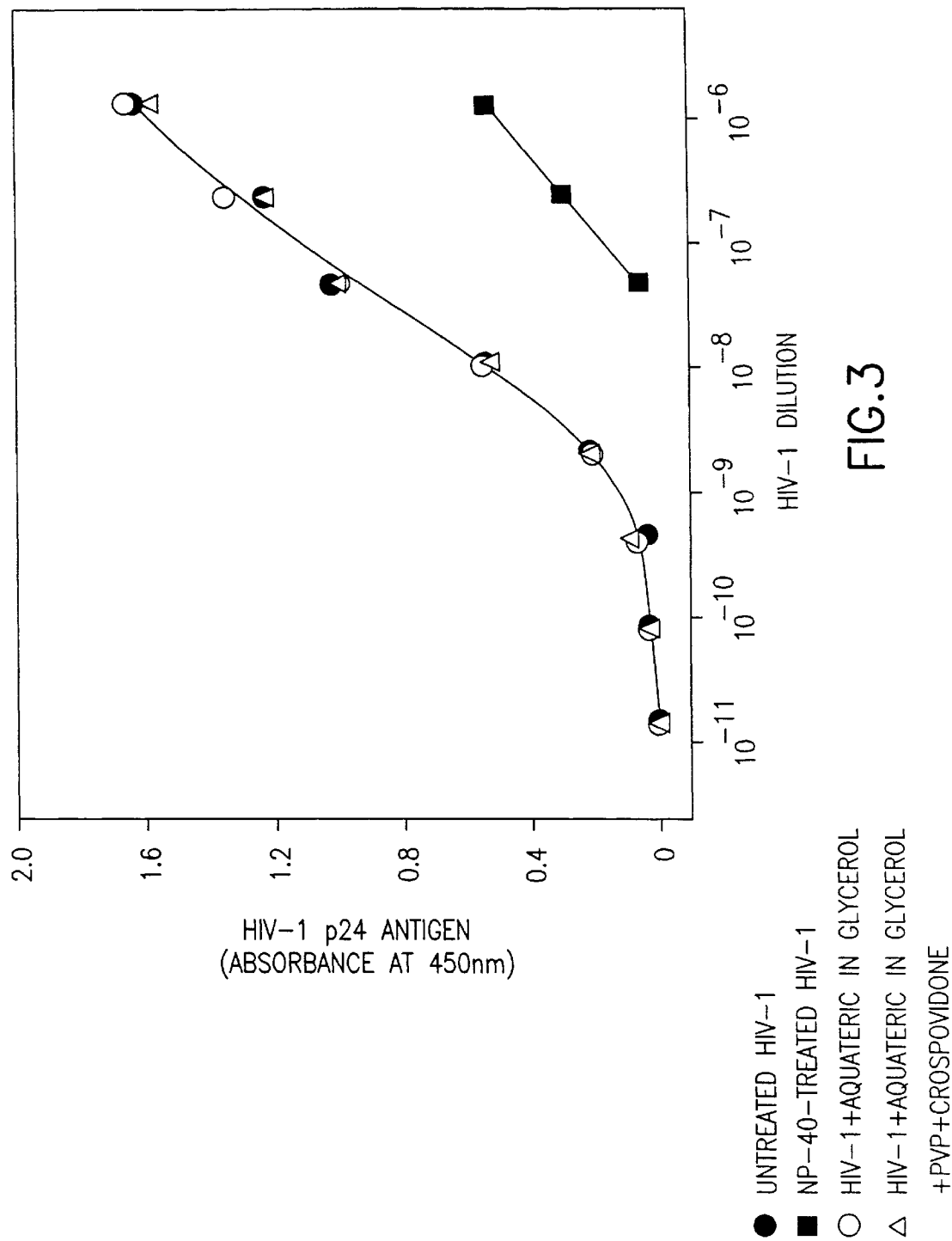
FIG. 3 is a graph of HIV-1 p24 antigen (absorbance at 450 nm) vs. HIV-1 dilution.
Figure 4:
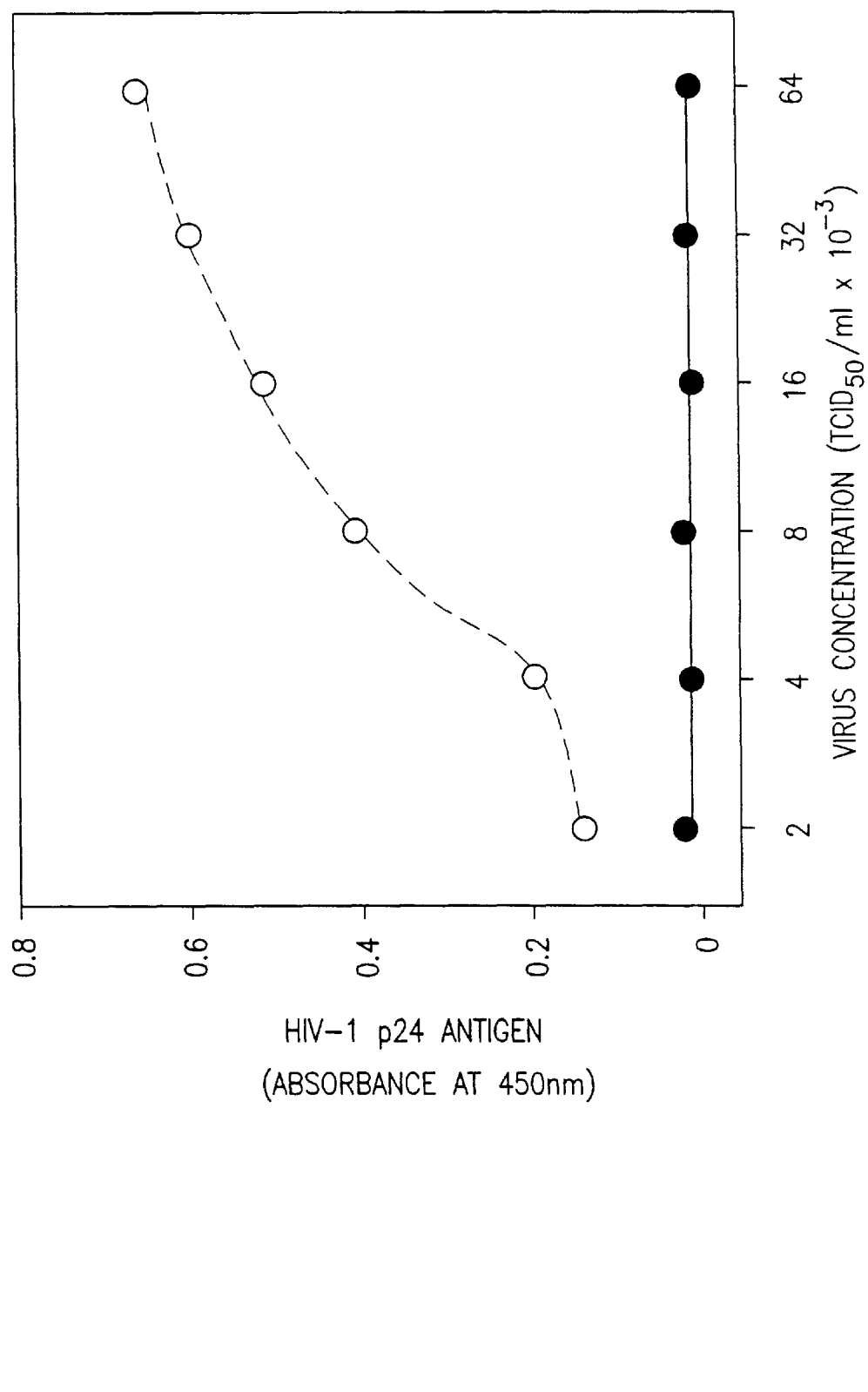
FIG. 4 is a graph of HIV-1 p24 antigen (absorbance at 450 nm) vs. virus concentration.

When a preparation of HIV-1 was mixed 1:1 with either an equal volume of a suspension of "AQUATERIC" in glycerol or with an equal volume of the above-mentioned formulation for 5 minutes at 37° C., a complete loss of HIV-1 infectivity occurred (FIG. 4). The inactivation of HIV-1 infectivity can be ascribed to the complete disruption of HIV-1 virions, as demonstrated by the quantitative release of the internal nucleocapsid antigen p24 (FIG. 3). Similarly, the infectivity of both HSV-1 and HSV-2 was destroyed by suspensions of "AQUATERIC" in glycerol or the "AQUATERIC"-glycerol formulation with PVP and Crospovidone (FIGS. 5 and 6).

With respect of FIG. 3, serial dilutions of untreated and treated HIV-1 were tested for p24 by ELISA. As a positive control, HIV-1 treated with the detergent NP40 was also tested. The results obtained with the "AQUATERIC"-glycerol formulation containing PVP and Crospovidone and NP40 were identical. The infectivity of HIV-1 was also eliminated by treatment with the "AQUATERIC"-glycerol formulation containing PVP and Crospovidone.

Figure 5:
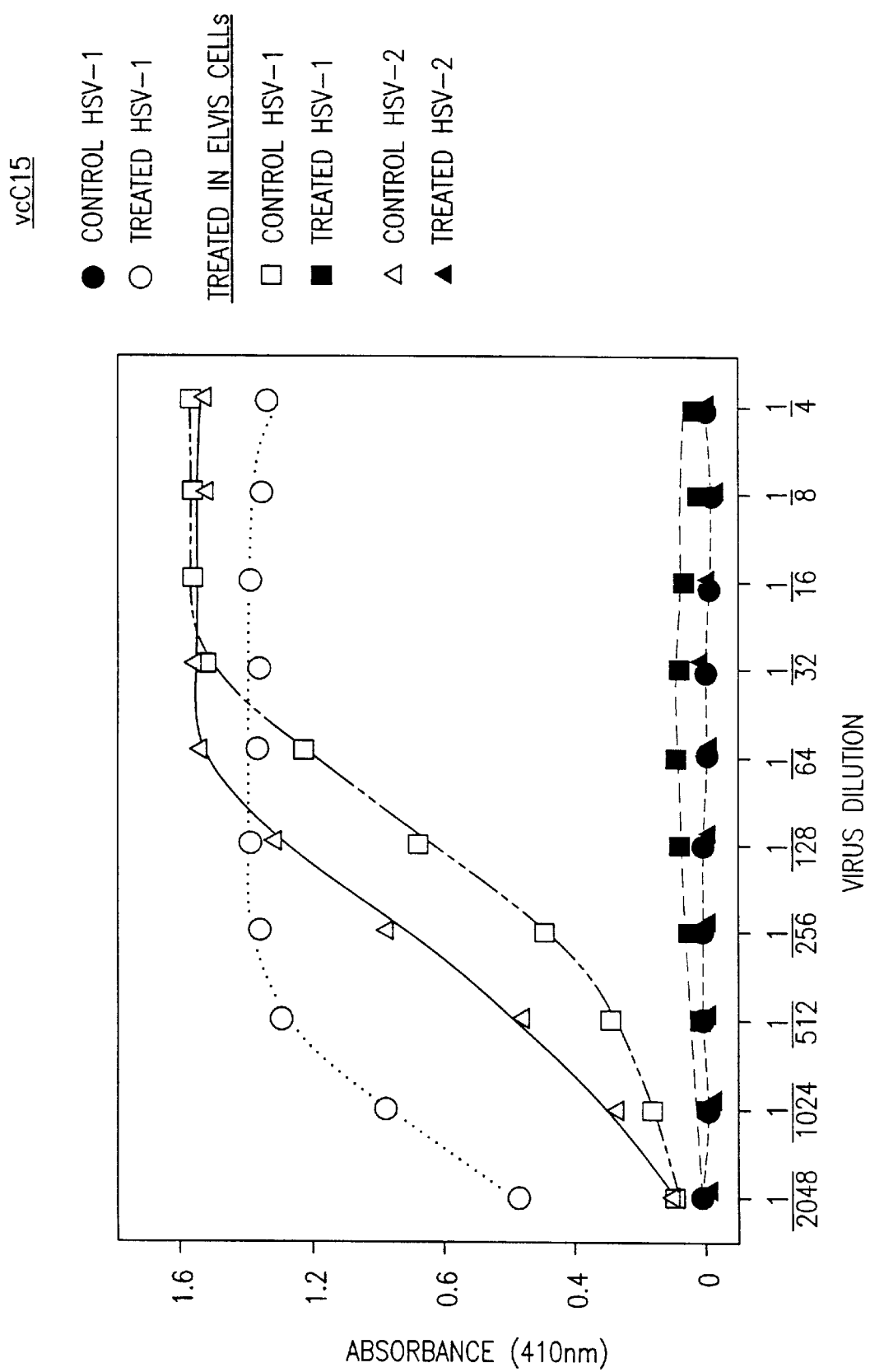
FIG. 5 is a graph of absorbance (410 nm) vs. virus dilution.

Concerning FIG. 5, serial dilutions of the virus preparations before or after treatment with "AQUATERIC" were tested for infectivity using two distinct readout systems based on quantitation of β-galactosidase (absorbance at 410 nm).

Figure 6:
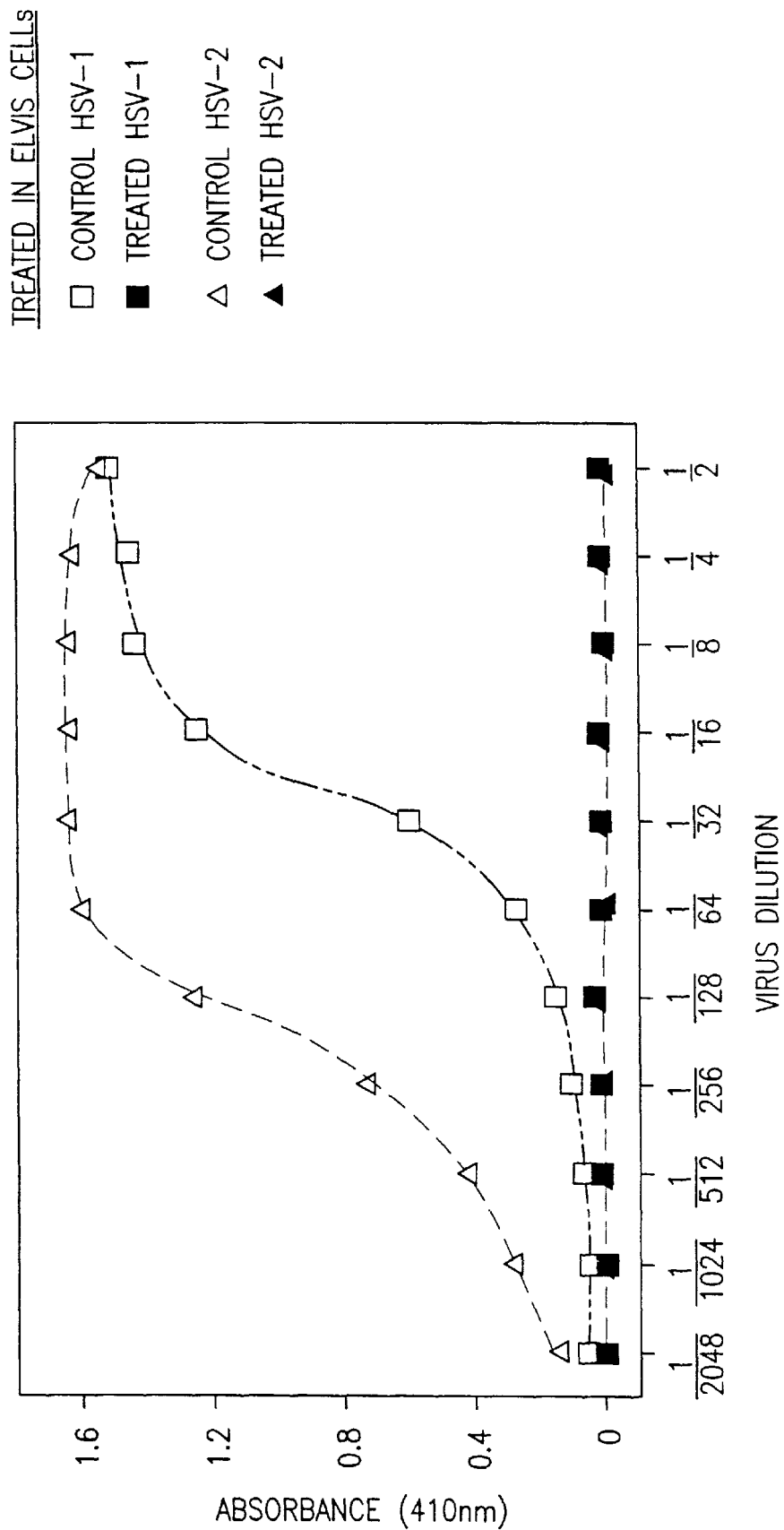
FIG. 6 is a graph of absorbance (410 nm) vs. virus dilution.

Regarding FIG. 6, virus preparations were mixed 1:1 with an "AQUATERIC"-glycerol formulation with PVP and Crospovidone for 5 minutes at 37° C. Serial dilutions of the virus preparations were tested for infectivity using a readout system based on quantitation of β-galactosidase (absorbance at 410 nm).

Thus, the micronization of CAP and its suspension in glycerol resulted in an active and stable formulation which has antiviral activity and is suitable for topical application to prevent the sexual transmission of HIV-1 and herpesviruses.

The aforementioned formulation of "AQUATERIC", PVP and Crospovidone in glycerol is suitable for topical application. However, in order to apply (administer) the formulation in predetermined quantities, in addition to the formulation, a measuring device, e.g., an applicator, should be provided.

It will be advantageous to incorporate the formulations containing CAP and/or HPMCP into hydroxypropyl methylcellulose capsules such as "VEGI CAPS" or "VEGGIE-CAPS", manufactured by GS Technologies, Springville, Utah, which can be configured as vaginal suppositories. This would reduce costs and avoid possible disposal problems. Such suppositories can be inserted into the vagina intact, whereby the shell of the capsule will soften and rupture upon interaction with moisture within the vagina, thus releasing the CAP and/or HPMCP formulation.

For example, the above-described hydroxypropyl methylcellulose capsules can be filled either with:

(a) "AQUATERIC" suspended in glycerol; or (b) "AQUATERIC" in solid form.

"AQUATERIC" in solid form, with or without additional inactive ingredients, can also be incorporated in gelatin capsules.

The formulation containing the active ingredient (CAP and/or HPMCP) of the present invention can be in the form of a single capsule or the formulation may be in the form of two or more capsules, each containing the same or distinct ingredients.

Example 4

Testing of anti-HIV-1, anti-HSV-1 and anti-HSV-2 Activity of Suppositories Containing "AQUATERIC", Hydroxypropyl Methylcellulose and Carbomer 974P Suppositories are prepared in such a way that 750 mg of "AQUATERIC" 100 mg of hydroxypropyl methylcellulose and 50 mg of Carbomer 974P are present in a single suppository prepared in a plastic mold provided by Paddock Laboratories, Minneapolis, Minn. The weight of a single suppository should be determined. An appropriate aliquot of the suppository is prepared by cutting it. Subsequently, the solid aliquot is melted at 37° C. just before the experiment is started. HIV-1-(or HSV-1- or HSV-2-) infected tissue culture material (if necessary preconcentrated), prewarmed to 37° C., is added to the melted suppository. The volume of the virus containing material should correspond to 4.5 ml per weight of a single suppository. The mixture of prewarmed virus material and melted suppository should be incubated for 5 minutes at 37° C., under vigorous mixing during this incubation period. Subsequently, the mixture is cooled to 4° C. and centrifuged. The middle liquid portion (the suppository base is expected to flow to the top and the suspended undissolved "AQUATERIC" is expected to pellet) is withdrawn and neutralized (pH about 7). Serial dilutions (undiluted and subsequent two-fold dilutions; the number of dilution steps depending on the predetermined titer of the respective virus) are added to cells. The infectivity is determined by measuring CPE and p24 antigen production for HIV-1, and by measuring β-galactosidase for HSV-1 and HSV-2. Concerning herpesviruses, the infectivity test should be carried out on ELVIS cells and an experiment using HSV-1 vgC15 can also be carried out. As a positive control, dilutions of the original virus materials should be tested for infectivity in a similar fashion. It is expected that the virus material will not be essentially diluted after contact with the lipid-based suppository.

Sodium bicarbonate can be added as an additional ingredient to make the suppositories effervescent and allow for the topical spreading of all ingredients.

It will be appreciated that the instant specification is set forth by way of illustration and not limitation, and that various modifications and changes may be made without departure from the spirit and scope of the present invention.

What is claimed is:

1. A method for decreasing the frequency of transmission of a virus selected from the group consisting of human immunodeficiency virus and herpesvirus, comprising administering to a human an effective anti-human immunodeficiency virus amount or anti-herpesvirus amount of at least one cellulose phthalate selected from the group consisting of cellulose acetate phthalate and hydroxypropyl methylcellulose phthalate, either alone or in combination with a pharmaceutically acceptable carrier or diluent.

2. The method of claim 1, wherein the at least one cellulose phthalate is cellulose acetate phthalate.

3. The method of claim 1, wherein the at least one cellulose phthalate is hydroxypropyl methylcellulose phthalate.

4. The method of claim 1, wherein said cellulose phthalate is a combination of cellulose acetate phthalate and hydroxypropyl methylcellulose phthalate.

5. The method of claim 2, wherein the virus is HIV-1.

6. The method of claim 3, wherein the virus is HIV-1.

7. The method of claim 4, wherein the virus is HIV-1.

8. The method of claim 2, wherein the virus is a herpesvirus.

9. The method of claim 8, wherein the herpesvirus is HSV-1.

10. The method of claim 8, wherein the herpesvirus is HSV-2.

11. The method of claim 3, wherein the virus is a herpesvirus.

12. The method of claim 11, wherein the herpesvirus is HSV-1.

13. The method of claim 11, wherein the herpesvirus is HSV-2.

14. The method of claim 4, wherein the virus is a herpesvirus.

15. The method of claim 14, wherein the herpesvirus is HSV-1.

16. The method of claim 14, wherein the herpesvirus is HSV-2.

17. The method of claim 1, wherein the administering is by topical administration.

18. A pharmaceutical composition for decreasing the frequency of transmission of a virus selected from the group consisting of human immunodeficiency virus and herpesvirus, comprising an effective anti-human immunodeficiency virus or anti-herpes virus amount of at least one cellulose phthalate selected from the group consisting of cellulose acetate phthalate and hydroxypropyl methylcellulose phthalate, in combination with a pharmaceutically acceptable carrier or diluent, wherein the at least one cellulose phthalate is in a micronized form comprising particles of a mean particle size of less than 35 microns, said particles being in a suspended form.

19. The pharmaceutical composition of claim 18, wherein said cellulose phthalate is a combination of cellulose-acetate phthalate and hydroxypropyl methylcellulose phthalate.

20. The pharmaceutical composition of claim 18, wherein the at least one cellulose phthalate is suspended in water or a saline solution and the at least one cellulose phthalate is cellulose acetate phthalate.

21. A method for decreasing the frequency of transmission of a virus selected from the group consisting of human immunodeficiency virus and herpesvirus, comprising administering to a human a suspension containing an effective anti-human immunodeficiency virus amount or anti-herpesvirus amount of at least one cellulose phthalate selected from the group consisting of cellulose acetate phthalate and hydroxypropyl methylcellulose phthalate.

22. The method of claim 21, wherein said at least one cellulose phthalate is in micronized form and is suspended in a water miscible, essentially anhydrous non-solvent for cellulose acetate phthalate or hydroxypropyl methycellulose phthalate.

23. The method of claim 22, wherein the micronized form comprises particles of a mean particle size of less than 35 microns.

24. The method of claim 22, wherein the micronized form comprises particles of a mean particle size of less than 5 microns.

25. The method of claim 22, wherein said non-solvent is glycerol.

26. The method of claim 21, wherein said at least one cellulose phthalate is in micronized form and is suspended in water.

27. The method of claim 21, wherein said at least one cellulose phthalate is in micronized form and is suspended in a saline solution.

28. The method of claim 25, wherein the micronized form comprises particles of a mean particle size of less than 35 microns.

29. The method of claim 28, wherein said suspension further comprises an $\alpha$-hydro-$\omega$-hydroxy poly(oxyethylene) poly(oxypropylene) poly(oxyethylene) block copolymer and distilled acetylated monoglycerides.

30. The method of claim 29, wherein said suspension further comprises polyvinyl pyrrolidone and a 1-ethenyl-2-pyrrolidinone homopolymer.

31. The method of claim 21, wherein the at least one cellulose phthalate is contained in a hydroxypropyl methylcellulose capsule.

32. The pharmaceutical composition of claim 18, wherein the micronized form comprises particles of a mean particle size of less than 5 microns and the at least one cellulose phthalate is hydroxypropyl methylcellulose phthalate.

* * * * *